US006884596B2

(12) United States Patent
Civelli et al.

(10) Patent No.: US 6,884,596 B2
(45) Date of Patent: Apr. 26, 2005

(54) SCREENING AND THERAPEUTIC METHODS FOR PROMOTING WAKEFULNESS AND SLEEP

(75) Inventors: Olivier Civelli, Irvine, CA (US); Steven Lin, Upland, CA (US)

(73) Assignee: The Regents of the University of California, Oakland, CA (US)

( * ) Notice: Subject to any disclaimer, the term of this patent is extended or adjusted under 35 U.S.C. 154(b) by 107 days.

(21) Appl. No.: 09/932,161

(22) Filed: Aug. 17, 2001

(65) Prior Publication Data

US 2002/0037533 A1 Mar. 28, 2002

Related U.S. Application Data

(63) Continuation-in-part of application No. 09/560,915, filed on Apr. 28, 2000, now Pat. No. 6,383,764.

(51) Int. Cl.$^7$ ...................... G01N 33/53; G01N 33/566; G01N 33/567; A61K 38/00
(52) U.S. Cl. ............................ 435/7.8; 435/7.2; 514/2; 436/501; 436/503
(58) Field of Search ...................... 435/7.8, 7.1; 514/2, 514/21, 44; 436/501, 567; 424/130.1; 530/300, 350, 399

(56) References Cited

U.S. PATENT DOCUMENTS

| 6,197,530 B1 | 3/2001 | Stricker-Krongrad et al. ........................ 435/7.21 |
| 6,323,177 B1 | * 11/2001 | Curran et al. ................... 514/8 |

FOREIGN PATENT DOCUMENTS

| WO | WO97/24436 | 7/1997 | ........... C12N/15/12 |
| WO | WO98/58962 | 12/1998 | .......... C07K/14/575 |
| WO | WO00/38704 | 6/2000 | ........... A61K/38/17 |
| WO | WO01/09182 | 2/2001 | .......... C07K/14/575 |

OTHER PUBLICATIONS

Wells, Additivity of Mutational Effects in Proteins. Biochemistry 29:8509–8517, 1990.*
Zhang et al. Effects of prolactin–releasing peptide (PRRP) on sleep regulation in rats. Society for Neuroscience Abstracts, 1999 vol. 25, No. 1–2, p. 1137. Meeting Info: Miami, Florida Oct. 23–28, 1999.*
Zhang et al. Abstract P80 "Prolactin–Releasing Peptide (PRRP) in Prolactin Release and Sleep–Wake Regulation," *Neuroimmunomodulation* 6:454 (1999).
Chen et al., "Prolactin–releasing peptide–immunoreactivity in A1 and A2 noradrenergic neurons of the rat medulla" *Brain Research*, 822:276–279 (1999).
Civelli et al., "Orphan receptors, novel neuropeptides and reverse pharmaceutical research" *Brain Research*, 848:63–65 (1999).

Danober et al., "Pathophysiological mechanisms of genetic absence epilepsy in the rat" *Progress in Neurobiol.*, 55:27–57 (1998).
Dong et al., "GRIP: a synaptic PDZ domain–containing protein that interacts with AMPA receptors" *Nature*, 386:279–284 (1997).
Dong et al., "Characterization of the glutamate receptor–interacting proteins GRIP1 and GRIP2" *J. of Neurosci.*, 19(16):6930–6941.
Egleton and Davis, "Bioavailability and transport of peptides and peptide drugs into the brain" *Peptides*, 18:1431–1439 (1997).
Fujii et al., "Tissue distribution of prolactin–releasing peptide (PrRP) and its receptor" *Regulatory Peptides*, 83:1–10 (1999).
Fujimoto et al., "Isolation and characterization of a novel bioactive peptide, carassius RFamide (C–RFa), from the brain of the Japanese crucian carp" *Biochem. & Biophysic. Research Comm.*, 242:436–440 (1998).
Hinuma et al., "A prolactin–releasing peptide in the brain" *Nature*, 393:272–276 (1998).
Horwell, "The 'peptoid' approach to the design of the non–peptide, small molecule agonists and antagonists of neuropeptides" *Trends Biotechnol.*, 13:132–134 (1995).
Iwasa et al., "Altered expression levels of G protein subclass mRNAs in various seizure stages of the kindling model" *Brain Research*, 818:570–574 (1999).
Kieber–Emmons et al., "Therapeutic peptides and peptidomimetics" *Current Opinion in Biotechnology*, 8:435–441 (1997).
Lin et al., "Prolactin releasing peptide (PRRP) suppresses absence seizures by modulating neuortransmission through AMPA receptors" *Society for Neuorscience, 29$^{th}$ Annual Meeting, Oct. 23–28, 1999*, Abstract 387.6 (1999).

(Continued)

Primary Examiner—Elizabeth Kemmerer
Assistant Examiner—Regina M. DeBerry
(74) Attorney, Agent, or Firm—McDermott Will & Emery LLP

(57) ABSTRACT

The invention provides methods of screening for a compound for promoting wakefulness in a mammal. The method is practiced by providing a compound that is a PrRP receptor agonist and determining the ability of the compound to promote wakefulness. Also provided by the invention are methods of screening for a compound for promoting sleep in a mammal. The methods are practiced by providing a compound that is a PrRP receptor antagonist and determining the ability of the compound to promote sleep. In addition, the invention provides a method of promoting wakefulness in a mammal. The method is practiced by administering to a mammal an effective amount of a PrRP receptor agonist. The invention further provides a method of promoting sleep in a mammal. The method is practiced by administering to a mammal an effective amount of a PrRP receptor antagonist.

4 Claims, 7 Drawing Sheets

OTHER PUBLICATIONS

Liu et al., "Evidence for a critical role of GABAergic transmission within the thalamus in the genesis and control of absence seizures in the rat" *Brain Research*, 545:1–7 (1991).

Marchese et al., "Cloning and chromosomal mapping of three novel genes, GPR9, GPR10, and GPR14, encoding receptors related to interleukin 8, neuropeptide Y and somatostatin receptors" *Genomics*, 29:335–344 (1995).

Maruyama et al., "Immunocytochemical localization of prolactin–releasing peptide in the rat brain" *Endocrinology*, 140 (5):2326–2333 (1999).

Matsumoto et al., "Stimulation of prolactin release by prolactin–releasing peptide in rats" *Biochem. & Biophysic. Research Comm.*, 259:321–324 (1999).

Matsumoto et al., "Distribution and characterization of immunoreactive prolactin–releasing peptide (PrRP) in rat tissue and plasma" *Biochem. & Biophysic. Research Comm.*, 257:264–268 (1999).

McCormick and Bal, "Sleep and Arousal: Thalamocortical Mechanisms" *Annual Review of Neuroscience*, 20:185–215 (1997).

Minami et al., "Cellular localization of prolactin–releasing peptide messenger RNA in the rat brain" *Neuroscience Letters*, 266:73–75 (1999).

Roland et al., "Anatomical distribution of prolactin–releasing peptide and its receptor suggests additional functions in the central nervous system and periphery" *Endocrinology*, 140:5736–5745 (1999).

Snead, O. Carter, "Evidence for G protein modulation of experimental–generalized absence seizures in rat" *Neuroscience Letters*, 148:15–18 (1992).

Srivastava et al., "Novel anchorage of GluR2/3 to the Postsynaptic density by the AMPA receptor–binding protein ABP" *Neuron*, 21:581–591 (1998).

Tsunoda et al., "A multivalent PDZ–domain protein assembles signalling complexes in a G–protein–coupled cascade" *Nature*, 338:243–249 (1997).

Vgontzas and Kales, "Sleep and its disorders," *Annu. Rev. Med.* 50:387–400 (1999).

Welch et al., "Sequence and tissue distribution of a candidate G–Coupled receptor cloned from rat hypothalamus" *Biochem. & Biophysic. Research Comm.*, 209 (2):606–613 (1995).

Wilson et al., "Orphan G–protein–coupled receptors: the next generation of drug targets?" *Brit. J. of Pharmacol.*, 125:1387–1392 (1998).

Xia et al., "Clustering of AMPA receptors by the synaptic PDZ domain–containing protein PICK1" *Neuron*, 22:179–187 (1999).

Zhang et al., "Sleep–Wake Mechanism, Effects of prolactin–releasing peptide (PrRP) on sleep regulation in rats," *Psychiatry and Clinical Neuroscience* 54:262–264 (2000).

* cited by examiner a

```
GPR10 tail      - FREELRKLLVAWPRKIAPHGQNMTVSVVI.
GluR2 tail      - NPSSSQNSQNFAATYREGYNYYGIESVKI.
GluR3 tail      - FKPAPATNTQNYATYREGYNVYGTESVKI.
``` b

GRIP (10 ug)       − + − + +
Flag GPR10 (ug)    5 0 1 2 5

IP: αFlag
Blot: αGRIP    117 —

Crude lysate
Blot: αGRIP    117 — c

1) Flag GPR10 WT -------- PHGQNMTVSVVI.
2) Flag GPR10 del6 ----- PHGQNM.
3) Flag GPR10 ΔLC ----- PHGQNMTVPRPA.
4) Flag GPR10 T365A --- PHGQNMAVSVVI.
5) Flag GPR10 V366A --- PHGQNMTASVVI.
6) Flag GPR10 S367A --- PHGQNMTVAVVI.
7) Flag GPR10 V368A --- PHGQNMTVSAVI.
8) Flag GPR10 V369A --- PHGQNMTVSVAI.
9) Flag GPR10 I370A --- PHGQNMTVSVVA.

e

Flag GPR10
┌ WT ┐ ┌ del6 ┐
1 2 3   1 2 3   1 2 3   1 2 3

48 —

——— IP ——— ——— Crude ———

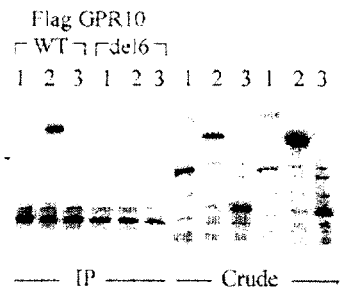

d

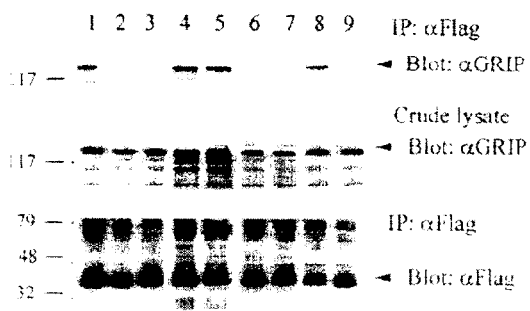

f

IP: αFlag
WT    +       +       +
del6     +       +       +

117 —
79 —

Blot: αGRIP   α-myc   α-myc

117 —
79 —

Crude   GRIP    ABP    PSD95
lysate

FIGURE 2

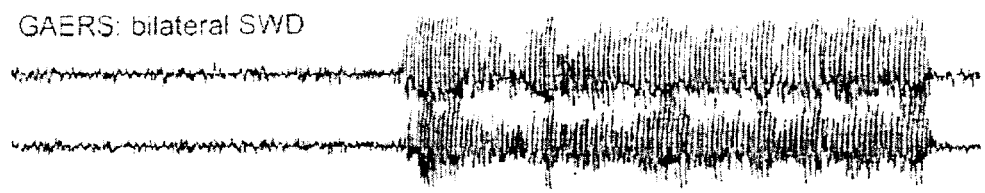
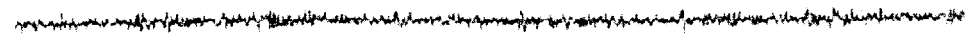
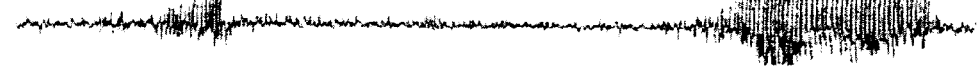
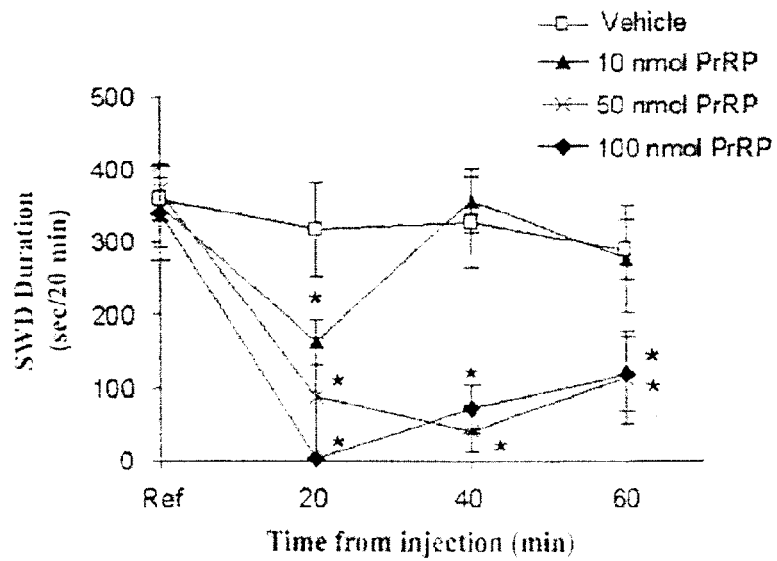
FIGURE 6 a. Pre-Infusion
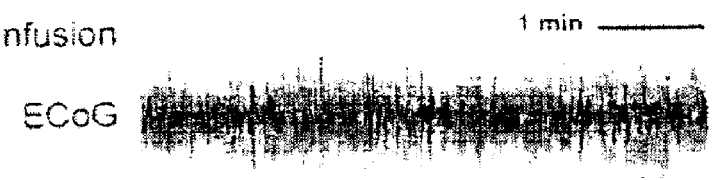
Post-Infusion
b.
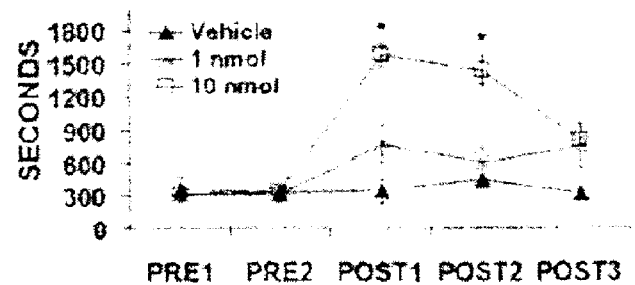
c.
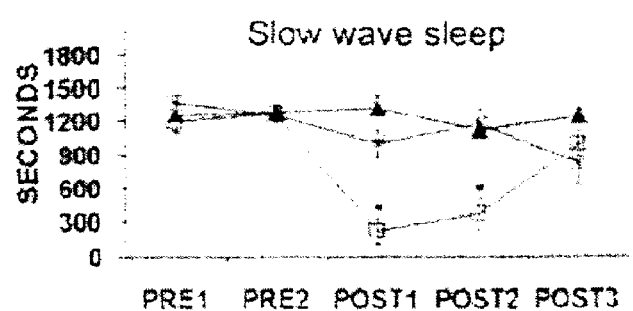
FIGURE 7

SCREENING AND THERAPEUTIC METHODS FOR PROMOTING WAKEFULNESS AND SLEEP

This application is a continuation-in-part of application U.S. Ser. No. 09/560,915, filed Apr. 28, 2000 now U.S. Pat. No. 6,383,764, which is incorporated herein by reference.

This invention was made with Government support under Grant No. MH60231, awarded by the National Institutes Of Health. The Government has certain rights in this invention.

BACKGROUND OF THE INVENTION

1. Field of the Invention

The present invention relates generally to the field of medicine and, more specifically, to therapeutic compositions and methods relating to Prolactin Releasing Peptide (PrRP).

2. Background Information

Sleep is a naturally occurring, periodic, reversible state of unconsciousness that is ubiquitous in mammals and birds, although its precise function is not known. The importance of sleep is suggested by its homeostatic regulation: the longer an animal is awake, the more it needs to sleep.

In humans, obtaining less than the required number of hours of sleep, particularly over several nights, leads to a decreased ability to retain new information, impaired productivity, altered mood, lowered resistance to infection and an increased susceptibility to accidents. Sleep-related traffic accidents annually claim thousands of lives, and operator fatigue has also been shown to play a contributory role in airplane crashes and other catastrophic accidents.

Besides lifestyle factors, a variety of physiological and psychological disorders can affect sleep patterns. The most common sleep disorder is primary insomnia, or a difficulty in initiating or maintaining sleep, which affects a large percentage of the population at some point in their lives. Other common sleep disorders include hypersomnia, or excessive daytime sleepiness, and narcolepsy, which is characterized by sudden and irresistible bouts of sleep.

Currently available drugs used to modulate wakefulness and sleep, such as drugs that induce sleep, prolong wakefulness, or enhance alertness, suffer from a number of shortcomings. For example, available sleep-inducing drugs often do not achieve the fully restorative effects of normal sleep. Often such drugs cause undesirable effects upon waking, such as anxiety or continued sedation. Furthermore, many of the currently available drugs that modulate sleep and wakefulness are addictive or have adverse effects on learning and memory.

Thus, there exists a need to identify new therapeutic agents that can be used to promote wakefulness and sleep. The present invention satisfies these needs and provides related advantages as well.

SUMMARY OF THE INVENTION

The invention provides methods of screening for a compound for promoting wakefulness in a mammal. The method is practiced by providing a compound that is a PrRP receptor agonist and determining the ability of the compound to promote wakefulness.

In one embodiment, the method is practiced by providing a compound that promotes a predetermined signal. The compound is identified by contacting a PrRP receptor with one or more candidate compounds under conditions wherein PrRP promotes a predetermined signal, and identifying a compound that promotes the predetermined signal.

In another embodiment, the method is practiced by providing a compound that binds to PrRP receptor. The compound is identified by contacting a PrRP receptor with one or more candidate compounds under conditions wherein PrRP binds to the PrRP receptor and identifying a compound that binds to PrRP receptor.

In a further embodiment, the method is practiced by providing a compound that promotes interaction of PrRP receptor with an AMPA receptor associated protein. The compound is identified by contacting a PrRP receptor with one or more candidate compounds under conditions wherein PrRP promotes interaction of PrRP receptor with an AMPA receptor associated protein and identifying a compound that promotes this interaction.

The invention also provides a method of promoting wakefulness in a mammal. The method is practiced by administering to a mammal an effective amount of a PrRP receptor agonist.

The invention further provides methods of screening for a compound for promoting sleep in a mammal. The methods are practiced by providing a compound that is a PrRP receptor antagonist and determining the ability of the compound to promote sleep.

In one embodiment, the method is practiced by providing a compound that reduces a predetermined signal. The compound is identified by contacting a PrRP receptor with one or more candidate compounds under conditions wherein a PrRP promotes a predetermined signal and identifying a compound that reduces the predetermined signal.

In another embodiment, the method is practiced by providing a compound that reduces binding of a PrRP receptor agonist to PrRP receptor. The compound is identified by contacting a PrRP receptor with one or more candidate compounds under conditions wherein PrRP binds to said PrRP receptor and identifying a compound that reduces binding of the PrRP receptor agonist to PrRP receptor.

In a further embodiment, the method is practiced by providing a compound that promotes interaction of PrRP receptor with an AMPA receptor associated protein. The compound is identified by contacting a PrRP receptor with one or more candidate compounds under conditions wherein PrRP promotes interaction of PrRP receptor with an AMPA receptor associated protein and identifying a compound that reduces the interaction.

The invention further provides a method of promoting sleep in a mammal. The method is practiced by administering to a mammal an effective amount of a PrRP receptor antagonist.

BRIEF DESCRIPTION OF THE DRAWINGS

FIG. 2A shows an alignment of the amino acid sequence of the cytoplasmic tail of GPR10 (SEQ ID NO:1) with the cytoplasmic tails of the AMPA receptor subunits GluR2 (SEQ ID NO:2) and GluR3 (SEQ ID NO:3).

FIG. 2B, top, shows an analysis of co-immunoprecipitation of GRIP with Flag-tagged GPR10 from transiently co-transfected HEK 293T cells. FIG. 2B, bottom, shows GRIP expression in the crude lysate.

FIG. 2C shows the C-terminal sequences of Flag GPR10 WT (SEQ ID NO:4) and its various mutations having the following sequence identifiers: del6 (SEQ ID NO:5); ΔLC (SEQ ID NO:6); T365A (SEQ ID NO:7); V366A (SEQ ID NO:8); S367A (SEQ ID NO:9); V368A (SEQ ID NO:10); V369A (SEQ ID NO:11); and I370A (SEQ ID NO:12).

FIG. 2D, top, shows an analysis of co-immunoprecipitation of GRIP with Flag-tagged GPR10 mutants from transiently co-transfected HEK 293T cells. FIG. 2D, middle, shows GRIP expression in the crude lysate. FIG. 2D, shows GPR10 expression in the co-immunoprecipitated samples.

FIG. 2E shows an analysis of co-immunoprecipitation of various 6X-His tagged GRIP PDZ domain polypeptides with wild-type or C-terminally deleted (del6) forms of Flag-tagged GPR10.

FIG. 2F, top, shows an analysis of co-immunoprecipition of transiently transfected GRIP, myc-tagged ABP or myc-tagged PSD95 with Flag-tagged GPR10 from HEK 293T cells stably expressing wild-type or del6 forms of Flag-tagged GPR10. FIG. 2F, bottom, shows expression of the indicated proteins in crude lysates.

FIG. 6A shows representative EEG with bilateral fronto-parietal spike and wave discharges in a GAERS prior to PrRP injection.

FIG. 6B shows changes in EEG pattern after i.c.v. injection of PrRP (100 nmol).

FIG. 6C shows cumulative duration of spike and wave discharges (SWD) at 20 min intervals in GAERS (mean±S.E.M.) before injection (Ref) and 20, 40, and 60 min after injection of vehicle or 10, 50, or 100 nmol PrRP. *$P<0.001$.

FIG. 7A shows the effect of PrRP on EEG and EMG activity.

FIG. 7B shows the effect of PrRP on total time spent awake.

FIG. 7C shows the effect of PrRP on slow wave sleep.

DETAILED DESCRIPTION OF THE INVENTION

Figure 1:
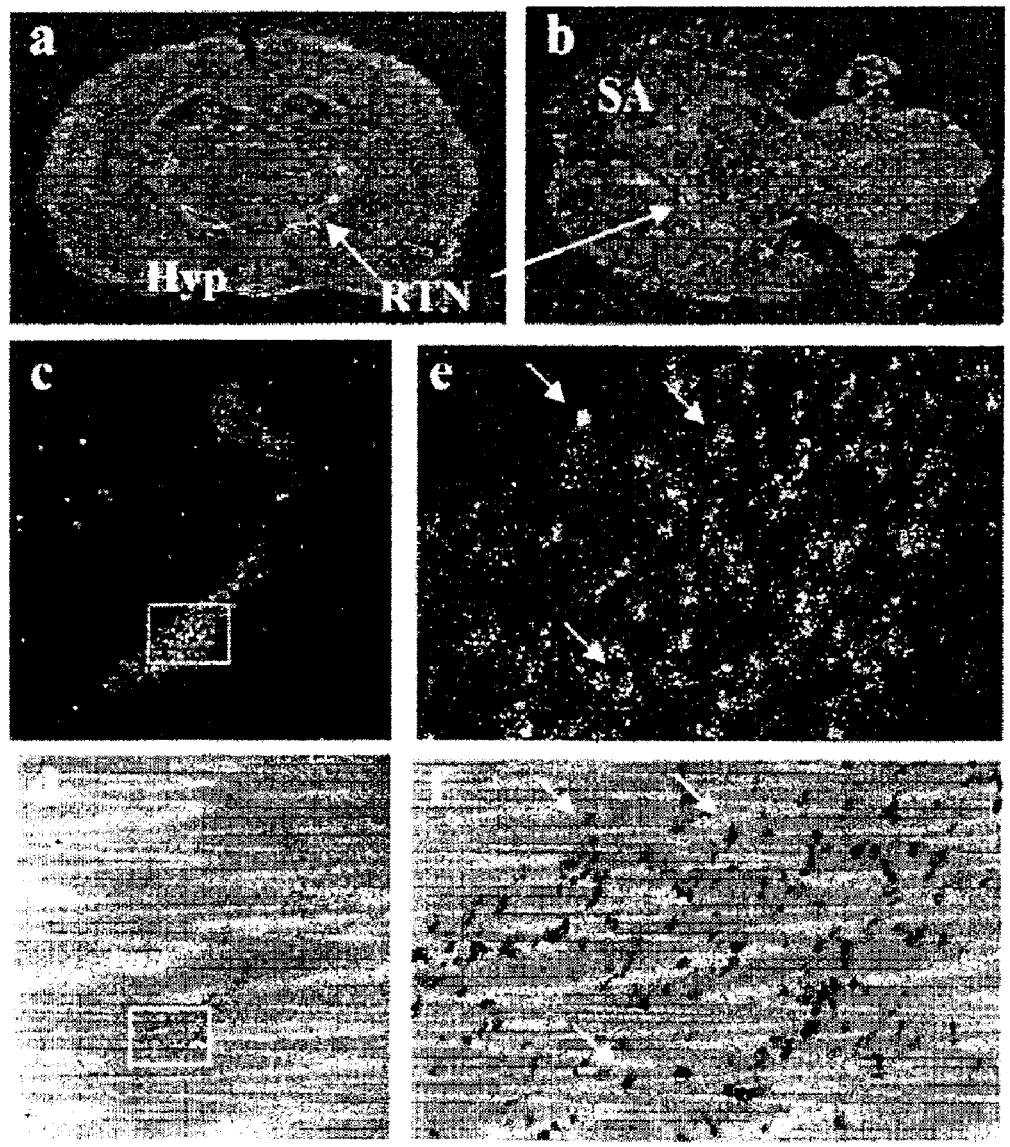
FIGS. 1A and 1B show expression of GPR10 RNA on coronal and horizontal sections, respectively, of adult rat brains. Abbreviations are RTN: reticular thalamic nucleus; Hyp: Hypothalamic nuclei; SA: Shell, nucleus accumbens.
FIG. 1C shows expression of GPR10 RNA within the RTN.
FIG. 1D shows labeling of GABAergic neurons within the section of the RTN in FIG. 1C.
FIGS. 1E and 1F show higher magnification views of FIGS. 1C and 1D, respectively.

The present invention relates to the determination that PrRP receptor modulation alters the activity of the reticular thalamic nucleus (RTN), a region of the brain implicated in sleep rhythms, attention processing and absence seizures, through a functional interaction between the PrRP receptor (GPR10), and Alpha-amino-3-hydroxy-5-methyl-4-isoxazolepropionic acid (AMPA) receptors. The inventors have determined that PrRP receptor activation in response to PrRP receptor agonists specifically reduces AMPA receptor mediated oscillatory activity in the RTN, effectively suppresses absence seizures in mammals. The inventors have further determined that agonist binding to PrRP receptor effectively promotes wakefulness in mammals.

Thus, based on the determination of an important pharmacological role of PrRP, and its underlying molecular mechanism, the invention provides compounds and related therapeutic methods for suppressing absence seizures and promoting wakefulness and sleep in mammals. The compounds and therapeutic methods of the invention can thus be used in the therapy of epilepsies and other diseases associated with absence seizures, and in promoting wakefulness and sleep in normal individuals and those having sleep disorders, such as insomnia and narcolepsy. Additionally, the invention provides methods of rapidly screening for compounds that modulate AMPA receptor signaling and compounds that control absence seizures and promote wakefulness and sleep. The compounds so identified will be useful in the control of absence seizures and promoting wakefulness and sleep, as well as in the prevention and treatment of conditions associated with tissues in which GPR10 is expressed, or in which known anti-epileptic drugs are effective.

In one aspect, the invention provides a method of controlling absence seizures. The method involves administering to a mammal susceptible to absence seizures an effective amount of a PrRP receptor agonist, such as PrRP or a functional analog thereof. As used herein, the term "mammal susceptible to absence seizures," refers to a human, veterinary animal or laboratory animal (e.g. non-human primate, rodent, feline or canine) that exhibits, can be induced to exhibit, or is at high risk of developing, absence seizures.

Absence seizures are brief attacks of impaired consciousness that can be distinguished from other forms of seizures both by their distinct electroencephalographic (EEG) patterns and by their response to pharmacological agents. By EEG, absence seizures are associated with bilateral synchronous and regular spike and wave discharges (SWD) with a frequency of 2.5 to 4 c/s, which start and end abruptly. Pharmacologically, absence seizures generally respond to the drugs ethosuximade, valproate and trimethadione, but are worsened by anti-convulsants such as carbamazepine and phenytoine which are effective in treating convulsive seizures.

In humans, several clinically recognized epilepsy syndromes, including childhood absence epilepsy, juvenile absence epilepsy, juvenile myoclonic epilepsy, myoclonic absence epilepsy, and eyelid myoclonia with absences, are associated with absence seizures. Epileptic syndromes are commonly classified according to the International Classification of Epileptic Syndromes proposed by the International League against Epilepsy in 1989.

Epidemiological studies have identified several predictive factors for the development of absence seizures, including past history of either febrile convulsions or generalized tonic-clonic seizures (GTCS), and family history of epilepsy or febrile convulsions (see, for example, Covanis et al., *Seizure* 1:281–289 (1992)). Because of the clear genetic predisposition for absence epilepsies, those skilled in the art understand that it will also be possible to determine susceptibility to absence seizures by genetic or biochemical profile.

Accordingly, a human "susceptible to absence seizures," can be a human exhibiting absence seizures, such as a human diagnosed with an epilepsy syndrome characterized by absence seizures, or a human considered to be at high risk of developing absence seizures.

A variety of non-human mammals that exhibit, or can be induced to exhibit, behavioral, electrographic and pharmacological characteristics of absence seizures in humans are known in the art. Such mammals are also considered herein to be "mammals susceptible to absence seizures." For example, Genetic Absence Epilepsy Rats from Strasbourg, or GAERS, exhibit behavioral and EEG patterns during spike and wave discharges (SWD) that are similar to those observed in humans during absence seizures (see Danober et al., *Prog. Neurobiol.* 55:27–57 (1998)). Other genetic models of absence epilepsy include the lethargic (lh/lh) mutant mouse (see Hosford et al., *Epilepsia* 38:408–414 (1997)), the WAG/Rij strain of rats (see Coenan et al., *Epilepsy Res.* 12:75–86 (1992)), and the tremor (tm/tm) mutant rat (Hanaya et al., *Epilepsia* 36:938–942 (1995)), which have been successfully used to predict or confirm the effects of a variety of anti-epileptic drugs in controlling absence seizures in humans.

Other relevant mammalian models of absence seizures in humans include pharmacological models, in which absence seizures are induced in laboratory animals, such as rodents, cats and primates, by administration of pentylenetetrazol, penicillin, gamma-hydroxybutyrate or GABA agonists (for a review, see Snead, *Epilepsia* 29:361–368 (1988)). Additionally, absence seizures can be induced in primates by thalamic stimulation (see, for example, David et al., *J. Pharmacol. Methods* 7:219–229 (1982)).

As used herein, the term "controlling," in relation to absence seizures, refers to a reduction in the frequency, duration, number or intensity of absence seizures in a treated mammal, as compared with the frequency, duration, number or intensity of absence seizures expected or observed without treatment. A determination of whether absence seizures are "controlled" by treatment can be made, for example, by direct observation, by self-reporting, or by examining on an EEG readout the frequency, duration, number or intensity or duration of spike and wave discharges (SWD)(see, for example, Example IV, below).

An amount of a pharmaceutical composition effective to control absence seizures is an amount effective to reduce the determined parameter (e.g. frequency, duration, number or intensity of absence seizures or SWD) by at least 10%. Preferably, the determined parameter will be reduced by at least 20%, more preferably at least 50%, such as at least 80%, in at least some treated mammals. Accordingly, a treatment that controls absence seizures will be useful in improving the quality of life in the treated mammals. Further description of effective amounts, formulations and routes of administration of the pharmaceutical compositions useful in the methods of the invention is provided below.

In another aspect, the invention provides a method of promoting wakefulness. The method involves administering to a mammal an effective amount of a PrRP receptor agonist. A mammal to be treated with a PrRP receptor agonist is generally in need of wakefulness and would benefit physically or psychologically from increased wakefulness. For example, increased wakefulness may be desired in an individual having sleepiness, a tendency to fall asleep, or having a sense of excessively deep sleep. A need for wakefulness can arise in an individual having or absent of a sleep-related disorder. For example, an individual may desire wakefulness to enhance performance in mental or physical activities, such as long distance driving, shift work and study. A need for wakefulness can also be caused by a disorder of excessive daytime sleepiness. Sleep apnea, narcoplepsy, idiopathic hypersomnia and psychogenic hypersomnia are examples of common disorders which lead to daytime sleepiness. Other causes of daytime sleepiness include, for example, sleep apnea, obesity, sleep deprivation, and adverse drug reactions.

Idiopathic hypersomnia is a disorder of excessive diurnal and nocturnal sleep characterized by virtually constant sleepiness, lengthy but nonrefreshing naps, prolonged night sleep, major difficulty with morning awakening, and sometimes sleep drunkeness. Idiopathic hypersomnia appears to have familial incidence and is associated with the presence of the HLA antigen HLA-DR5. Therefore, those skilled in the art will understand that it will be possible to determine susceptibility to hypersomnia by genetic or biochemical profile.

Narcolepsy is characterized by excessive daytime sleepiness, often with involuntary symptoms of reduced wakefulness including, for example, cataplexy, which is muscle weakness or paralysis in response to sudden emotion, sleep paralysis, which is the inability to move or call out when first awake, and hallucinations. Pharmacologically, treatment of narcolepsy involves separate treatments for sleep attacks and cataplexy. Epidemiological studies have identified several predictive factors for the development of narcolepsy, including a history of cataplexy. A genetic predisposition to narcolepsy can be indicated by the presence of HLA allele DQB1*0602. Therefore, those skilled in the art understand that it will be possible to determine susceptibility to narcolepsy by genetic or biochemical profile.

A variety of non-human mammals that exhibit, or can be induced to exhibit, behavioral, electrographic and pharmacological characteristics of narcolepsy in humans are known in the art. For example, canine narcolepsy is a naturally-occurring animal model of the human disorder (Riehl, et al., *Neuropsychopharmacology*, 23:34–35 (2000)). Canine models exhibit short sleep latency, fragmented sleep patterns, cataplexy and pharmacological characteristics similar to those observed in humans having narcolepsy. Canine models of narcolepsy have been successfully used to predict or confirm the effects of a variety of compounds for their effects on wakefulness, and to screen for new compounds for use as treatments for human narcolepsy.

Methods for diagnosing disorders of excessive daytime sleepiness are well known to those skilled in the art. Therefore, those skilled in the art will be able to determine individuals having sleep disorders that could benefit from treatment with a PrRP receptor agonist that promotes wakefulness. In addition, such treatment can be beneficial to individuals absent such sleep disorders when alertness, awareness, consciousness, or lack of sleep are desired.

As used herein, the term "promoting wakefulness" refers to a decrease in sleepiness, tendency to fall asleep, or other symptoms of undesired or reduced alertness or consciousness compared with sleepiness, tendency to fall asleep, or other symptoms of undesired or reduced alertness or consciousness expected or observed without treatment. Promoting wakefulness refers to a decrease in any stage of sleep, including light sleep, deeper sleep characterized by the presence of high amplitude, low wave brain activity termed "slow wave sleep", and rapid eye movement (REM) sleep. A compound that promotes wakefulness can, for example, cause the animal to wake from sleep, prolong periods of wakefulness, prolong normal latency to sleep, restore normal sleep patterns following sleep deprivation, or enhance beneficial wake-like characteristics, such as alertness, responsiveness to stimuli, and energy.

In a further aspect, the invention provides a method of promoting sleep by administering an effective amount of a PrRP receptor antagonist. A mammal to be treated with a PrRP receptor antagonist is generally in need of sleep and could benefit physically or psychologically from increased quality or quantity of sleep. For example, a mammal having reduced or insufficient quality or quantity of sleep, such as reduced ability to fall asleep or stay asleep, having the tendency to awaken earlier than desired in the morning or having a sense of light or unrefreshing sleep can be considered to be in need of sleep.

A variety of physical and psychological conditions can lead to reduced quality or quantity of sleep in an individual. For example, insomnias such as adjustment sleep disorder and psychophysiologic insomnia; sleep disorders such as periodic limb movement disorder and restless legs syndrome; circadian rhythm disorders such as circadian rhythm sleep disorder and delayed sleep phase syndrome, are common causes of reduced quality or quantity of sleep. In addition, medical and psychiatric conditions, such as chronic pain and depression, can cause reduced quality or quantity of sleep. Further, medications used for treating a variety of conditions can cause reduced quality or quantity of sleep. Examples of such medications include β-blockers, corticosteroids, bronchodilators, selective serotonin reuptake inhibitors and thyroid hormone.

As used herein, the term "promoting sleep" refers to increasing the quality or quantity of sleep. For example, promoting sleep can increase the ability to fall asleep or stay sleep, increase the number of hours slept prior to waking and increasing the perceived depth or refreshing effect of sleep. A compound that promotes sleep can, for example, cause the animal to sleep, prolong periods of sleep, promote restful sleep, decrease sleep latency, or decrease unwanted wake-like characteristics, such as anxiety and hyperactivity.

Methods for diagnosing insomnia and related disorders of reduced sleep are well known to those skilled in the art. Therefore, those skilled in the art will be able to determine individuals having sleep disorders that could benefit from treatment with a PrRP receptor antagonist that promotes sleep. In addition, such treatment can be beneficial to individuals absent such sleep disorders when an increase in quality or quantity of sleep is desired.

A determination of whether wakefulness or sleep is promoted by treatment can be made, for example, by direct observation of behavioral or physiological properties of mammalian sleep, by self-reporting, or by various well-known methods, including electrophysiological methods. Such methods include, for example, examining electroencephalograph (EEG) activity amplitude and frequency patterns, referred to herein as "EEG measurement;" examining electromyogram activity, referred to herein as "EMG measurement;" and examining the amount of time during a measurement time period, in which a mammal is awake or exhibits a behavioral or physiological property characteristic of wakefulness, referred to herein as "wake time measurement."

PrRP was originally identified as a peptide having the physiological role of promoting the release of prolactin, a hormone involved in mammary development and lactation, from the anterior pituitary (Hinuma et al., Nature 393:272–276 (1998)).

As used herein, the term "PrRP receptor agonist" refers to a compound that selectively promotes or enhances normal signal transduction through the PrRP receptor. A PrRP receptor agonist can act by any agonistic mechanism, such as by binding a PrRP receptor at the normal PrRP binding site, thereby promoting PrRP receptor signaling. A PrRP receptor agonist can also act, for example, by potentiating the binding activity of PrRP or signaling activity of PrRP receptor. The methods of the invention can advantageously be used to identify a PrRP receptor agonist that acts through any agonistic mechanism. As described herein, an example of a PrRP receptor agonist is a "PrRP." A PrRP agonist can also be a "PrRP functional analog," as described below.

As used herein, the term "PrRP" refers to a peptide having identity with at least 5 residues of the native sequence of a mammalian prolactin-releasing peptide (PrRP), and which binds a "PrRP receptor" with an affinity (Kd) of about $10^{-5}$ M or less. A PrRP of the invention can thus have identity with at least 5, 6, 7, 8, 9, 10, 15, 20 or more contiguous or non-contiguous amino acid residues of a native PrRP. Preferably, a PrRP of the invention binds a PrRP receptor with a Kd of about $10^{-6}$ M or less, more preferably about $10^{-7}$ M or less, most preferably about $10^{-8}$ M or less, including about $10^{-9}$ M or less, such as $10^{-10}$ M or less.

Mature, native PrRP peptides exist in at least two forms, a 31 amino acid peptide (PrRP-31) and a 20 amino acid peptide (PrRP-20), which are amidated at the carboxy-terminus. PrRP-31 and PrRP-20 are derived from a longer preproprotein. The purification of PrRP-31 and PrRP-20 from bovine hypothalamus, the cloning of PrRP preproprotein from bovine, rat and human, the characterization of PrRP-31 and PrRP-20 as peptides having prolactin-releasing activity towards rat anterior pituitary cells in vitro, and the importance of the C-terminal amide for PrRP activity, are described in Hinuma et al., Nature 393:272–276 (1998).

The amino acid sequences of PrRP-31 from bovine, rat and human are as follows:
Bovine: SRAHQHSMEIRTPDINPAWYAGRGIRPVGRF (SEQ ID NO:13)
Rat: SRAHQHSMETRTPDINPAWYTGRGIRPVGRF (SEQ ID NO:14)
Human: SRTHRHSMEIRTPDINPAWYASRGIRPVGRF (SEQ ID NO:15)
The amino acid sequences of PrRP-20 from bovine, rat and human, which contain the C-terminal 20 amino acids of PrRP-31, are as follows:
Bovine: TPDINPAWYAGRGIRPVGRF (SEQ ID NO:16)
Rat: TPDINPAWYTGRGIRPVGRF (SEQ ID NO:17)
Human: TPDINPAWYASRGIRPVGRF (SEQ ID NO:18)
The term "PrRP" is intended to encompass PrRP-31 and PrRP-20 from bovine, rat and human, having the amino acid sequences shown above, as well as PrRP-31 and PrRP-20 from other mammalian species, including, for example, non-human primates, mouse, rabbit, porcine, ovine, canine and feline species. The sequences of PrRP from other mammalian species can be readily determined by those skilled in the art, for example either by purifying PrRP from hypothalamic extracts, or by cloning PrRP preproproteins, following the methods described in Hinuma et al., *Nature* 393:272–276 (1998). Because of the high degree of identity between bovine, rat and human sequences, it is expected that PrRP from other mammalian species will be substantially similar in structure and function to the known PrRP sequences.

The term "PrRP" is also intended to encompass peptides that are longer or shorter than PrRP-31 or PrRP-20, so long as they have identity with at least 5 residues of the native sequence of a mammalian prolactin-releasing peptide (PrRP), and can bind the PrRP receptor GPR10 with an affinity (Kd) of less than about $10^{-5}$ M. Thus, the term "PrRP" encompasses peptides that have one or several amino acid additions or deletions compared with the amino acid sequence of a PrRP-31 or PrRP-20. Those skilled in the art recognize that such modifications can be desirable in order to enhance the bioactivity, bioavailability or stability of the PrRP, or to facilitate its synthesis or purification.

The term "PrRP" is further intended to encompass peptides having identity with at least 5 residues of the native sequence of a mammalian prolactin-releasing peptide (PrRP), which bind a PrRP receptor with an affinity (Kd) of about $10^{-5}$ M or less, and which have one or several minor modifications to the native PrRP sequence. Contemplated modifications include chemical or enzymatic modifications (e.g. acylation, phosphorylation, glycosylation, etc.), and substitutions of one or several amino acids to a native PrRP sequence. Those skilled in the art recognize that such modifications can be desirable in order to enhance the bioactivity, bioavailability or stability of the PrRP, or to facilitate its synthesis or purification.

Contemplated amino acid substitutions to the native sequence of a PrRP include conservative changes, wherein a substituted amino acid has similar structural or chemical properties (e.g., replacement of an apolar amino acid with another apolar amino acid; replacement of a charged amino acid with a similarly charged amino acid, etc.). Those skilled in the art also recognize that nonconservative changes (e.g., replacement of an uncharged polar amino acid with an apolar amino acid; replacement of a charged amino acid with an uncharged polar amino acid, etc.) can be made without affecting the function of PrRP. Furthermore, non-linear variants of a PrRP sequence, including branched sequences and cyclic sequences, and variants that contain one or more D-amino acid residues in place of their L-amino acid counterparts, can be made without affecting the function of PrRP.

In particular, the term "PrRP" is intended to encompass peptides having minor modifications to the native PrRP sequence that serve to increase its penetration through the blood-brain barrier (BBB). For a review of strategies for increasing bioavailability of peptides and peptide drugs in the brain, and of methods for determining the permeability of peptides through the BBB using in vitro and in vivo assays, see Engleton et al., *Peptides* 9:1431–1439 (1997).

Strategies that have been successfully used to increase the permeability of other neuropeptides through the BBB are particularly contemplated. For example, modifying the opioid peptide analgesic Met-enkephalin with D-penicillamine at two positions, forming a disulfide bridge that conformationally constrains the peptide, dramatically increases its stability towards BBB endothelial cell proteases and its BBB permeability. Likewise, linking two enkephalin peptides, each containing a D-amino acid residue at the second position, with a hydrazide bridge, results in a metabolically stable peptide with improved brain penetration. Additionally, halogenation of an enkephalin peptide has been shown to increase its BBB permeability. Similar modifications to PrRP peptides are likewise expected to be advantageous.

Additional modifications to a PrRP peptide that can increase its BBB penetration include conjugating the peptide to a lipophilic moiety, such as a lipophilic amino acid or methyldihydropyridine. PrRP peptide can also be conjugated to a transporter, such as the monoclonal antibody OX26 which recognizes the transferrin receptor, or cationized albumin which utilizes the adsorptive mediated endocytosis pathway, so as to increase its BBB penetration.

Those skilled in the art can determine which residues and which regions of a native PrRP sequence are likely to be tolerant of modification and still retain the ability to bind PrRP receptor with high affinity. For example, amino acid substitutions, or chemical or enzymatic modifications, at residues that are less well conserved between species are more likely to be tolerated than substitutions at highly conserved residues. Accordingly, an alignment can be performed among PrRP sequences of various species to determine residues and regions in which modifications are likely to be tolerated.

Additional guidance for determining residues and regions of PrRP likely to be tolerant of modification is provided by studies of PrRP fragments and variants. For example, based on the observation that PrRP-20 has similar ability to transduce signals through the PrRP receptor as PrRP-31 (see, for example, Hinuma et al., *Nature* 393:272–276 (1998)), it is likely that the N-terminus of PrRP is highly tolerant of the modifications described herein.

In particular, as described in Roland et al., *Endocrinology* 140:5736–5745 (1999), a peptide designated PrRP(25–31), consisting of the C-terminal seven amino acids of PrRP (IRPVGRF, SEQ ID NO:23) binds GPR10 with an apparent affinity of 200 nM, compared with an affinity of about 1 nM for PrRP-31 or PrRP-20, and mobilizes calcium in CHOK1 cells transfected with GPR10. Thus, a peptide consisting of, or comprising, the amino acid sequence designated SEQ ID NO:23 is encompassed by the term "PrRP."

Alanine scanning mutagenesis of PrRP (25–31) indicates that variants with substitutions of Ile25, Pro27, Val28, or Phe31 retain the ability to bind GPR10 with an affinity of about $10^{-6}$ M. Thus, a PrRP can consist of, or comprise, the amino acid sequences XRPVGRF (SEQ ID NO:19), IRXVGRF (SEQ ID NO:20), IRPXGRF (SEQ ID NO:21), IRPVGRX (SEQ ID NO:22), where "X" is any amino acid, preferably a non-polar amino acid, more preferably alanine. Substitutions of Arg26 or Gly29 were shown to substantially reduce binding affinity of PrRP (25–31) for GPR10, and substitution of Arg30 completely eliminated binding. Substitution of either Arg26 or Arg30 with lysine or citrulline also completely eliminated binding. More generally, a PrRP peptide can be considered to consist of, or comprise, the amino acid sequence XRXXGRX, so long as it retains PrRP receptor binding activity.

In the modified PrRP sequences described above, the effect of amino acid substitutions on calcium signaling was commensurate with the effect on binding to GPR10 (see Roland et al., *Endocrinology* 140:5736–5745 (1999)). Accordingly, in view of the disclosure herein, it is predictable that a peptide considered-to be a "PrRP" by GPR10 binding criteria will also be functionally active in mediating G-protein coupled signaling through PrRP receptor, inhibiting AMPA mediated signaling in whole cell preparations, inhibiting oscillatory activity in RTN preparations, suppressing absence seizures in susceptible mammals, and preventing or treating neurological and psychiatric disorders in which PrRP-31 or PrRP-20 are effective. Thus, as described further below, a peptide having a modified PrRP sequence can be assayed by any of these functional criteria to confirm that it is a PrRP.

The PrRP peptides of the invention can be prepared in substantially purified form using either conventional peptide synthetic methods (see, for example, Roland et al., *Endocrinology* 140:5736–5745 (1999)), or using conventional biochemical purification methods, starting either from tissues containing PrRP or from recombinant sources (see, for example, Hinuma et al., *Nature* 393:272–276 (1998)).

As used herein, the term "PrRP receptor antagonist" refers to a compound that selectively inhibits or decreases normal signal transduction through the PrRP receptor. A PrRP receptor antagonist can act by any antagonistic mechanism, such as by binding a PrRP receptor or PrRP, thereby inhibiting binding between PrRP and PrRP receptor. A PrRP receptor antagonist can also act, for example, by inhibiting the binding activity of PrRP or signaling activity of PrRP receptor. For example, a PrRP receptor antagonist can act by altering the state of phosphorylation or glycosylation of PrRP receptor. The methods of the invention can advantageously be used to identify a PrRP receptor antagonist that acts through any antagonistic mechanism. A PrRP antagonist can be, for example, a "PrRP functional analog," as described below.

As used herein, the term "PrRP functional analog" refers to a molecule that binds the PrRP receptor GPR10 with an affinity (Kd) of about $10^{-5}$ M or less, and which is not encompassed within the definition of a "PrRP," as set forth above. Preferably, a PrRP functional analog will bind a PrRP receptor with a Kd of about $10^{-6}$ M or less, more preferably about $10^{-7}$ M or less, most preferably about $10^{-8}$ M or less, including about $10^{-9}$ M or less, such as about $10^{-10}$ M or less.

The PrRP functional analogs of the invention can act as PrRP receptor agonists, and thus be able to mediate the same biochemical and pharmacological effects (e.g. signal transduction through the PrRP receptor, reduction of AMPA receptor activity, suppression of absence seizures in mammals) as PrRP. A PrRP functional analog identified by the methods described herein can alternatively act as a PrRP receptor antagonist, and thus inhibit signaling through GPR10, prevent the suppression of AMPA receptor mediated activity, or both. Such antagonists can advantageously be used in therapeutic applications where a reduction in PrRP receptor signaling is desired, including in the treatment of sleep and attention disorders. PrRP functional analogs of the invention, which are themselves not appropriate for therapeutic use, can advantageously be used to optimize the design of effective therapeutic compounds, or used in the screening methods described herein as competitors.

A PrRP functional analog can be a naturally occurring macromolecule, such as a peptide, nucleic acid, carbohydrate, lipid, or any combination thereof. A PrRP functional analog also can be a partially or completely synthetic derivative, analog or mimetic of such a macromolecule, or a small organic or inorganic molecule prepared partly or completely by synthetic chemistry methods. A PrRP functional analog can be identified starting either by rational design based on the corresponding peptide, by functional screening assays, or by a combination of these methods.

PrRP functional analogs include peptidomimetics of PrRP, such as peptidomimetics of a peptide containing, or consisting of, the amino acid sequence set forth as SEQ ID NO:23. As used herein, the term "peptidomimetic" refers to a non-peptide agent that is a topological analog of the corresponding peptide. Those skilled in the art understand that the identified ability of PrRP-31, PrRP-20, PrRP(25–31) and of certain single amino acid variants of PrRP(25–31) to bind PrRP receptor with high affinity, provides sufficient structural and functional information to rationally design peptidomimetics of PrRP.

Such a peptidomimetic can, for example, retain some or all of the functional groups of the amino acids shown to be functionally important in the C-terminus of PrRP (such as the 3-guanylpropyl radical of Arg26 and Arg30, the hydrogen of Gly29, etc.). A peptidomimetic of PrRP can also, for example, consist partially or completely of a non-peptide backbone used in the art in the design of other peptidomimetics, such as a glucose scaffold, a pyrrolidinone scaffold, a steroidal scaffold, a benzodiazepine scaffold, or the like.

Methods of rationally designing peptidomimetics of peptides, including neuropeptides, are known in the art. For example, the rational design of three peptidomimetics based on the sulfated 8-mer peptide CCK26–33, and of two peptidomimetics based on the 11-mer peptide Substance P, and related peptidomimetic design principles, are described in Horwell, *Trends Biotechnol.* 13:132–134 (1995).

Individual, rationally designed peptidomimetics of PrRP peptides can be assayed for their ability to bind the PrRP receptor, or to induce signaling through the PrRP receptor, or both, using one or more of the assays described herein. Similarly, a plurality of peptidomimetic compounds, such as variants of a peptidomimetic lead compound, or a plurality of other compounds, can be assayed simultaneously or sequentially using the binding, signaling and pharmacological assays described herein.

In methods of controlling absence seizures, promoting wakefulness and sleep, and for certain other therapeutic applications, a PrRP functional analog can be used. In comparison to a PrRP peptide, a PrRP functional analog can be more stable, more active, or have higher inherent ability to penetrate the blood-brain barrier than a PrRP.

A candidate compound can be assayed to determine whether it is a PrRP agonist or antagonist, either by a signaling assay, a binding assay, or both. The number of different compounds to screen in a particular assay can be determined by those skilled in the art, and can be 2 or more, such as 5, 10, 15, 20, 50 or 100 or more different compounds. For certain applications, such as when a library of random compounds is to be screened, and for automated procedures, it may be desirable to screen $10^3$ or more compounds, such as $10^5$ or more compounds, including $10^7$ or more compounds.

Methods for producing large libraries of chemical compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.*, 2:363–371 (1998); Sofia, *Mol. Divers.* 3:75–94 (1998); Eichler et al., *Med. Res. Rev.* 15:481–496 (1995); and the like. Libraries containing large numbers of natural and synthetic compounds also can be obtained from commercial sources.

In one embodiment, a signaling assay can be performed to determine whether a candidate compound is a PrRP receptor agonist or antagonist. In such an assay, a PrRP receptor is contacted with one or more candidate compounds under conditions wherein the PrRP receptor produces a predetermined signal in response to a PrRP agonist, such as PrRP. In response to PrRP receptor activation, a predetermined signal can be an increase or a decrease from an unstimulated baseline signal. An example of a predetermined signal which increases from an unstimulated baseline signal is a detected second messenger molecule that is produced in response to PrRP receptor activation. An example of a predetermined signal which decreases from an unstimulated baseline signal is a detected second messenger molecule that is hydrolyzed in response to PrRP receptor activation. The production of a predetermined signal in response to PrRP receptor agonist binding to PrRP receptor can therefore be an increase in a predetermined signal which positively correlates with PrRP receptor activity, or a decrease in a predetermined signal which negatively correlates with PrRP receptor activity. Using a signaling assay of the invention, a PrRP receptor agonist is identified that promotes production of a predetermined signal, whether the agonist promotes an increase in a predetermined signal that positively correlates with PrRP receptor activity, or a decrease in a predetermined signal that negatively correlates with PrRP receptor activity.

Similarly, a signaling assay can be performed to determine whether a candidate compound in a PrRP receptor antagonist. In such an assay, a PrRP receptor is contacted with one or more candidate compounds under conditions wherein the PrRP receptor produces a predetermined signal in response to a PrRP agonist, such as PrRP, and a compound is identified that reduces production of the predetermined signal. The candidate compound can be tested at a range of concentrations to establish the concentration where half-maximal signaling occurs; such a concentration is generally similar to the dissociation constant (Kd) for PrRP receptor binding.

As used herein, the term "PrRP receptor," is intended to refer to a mammalian seven-transmembrane-domain G-protein coupled receptor, variously designated in the art "GPR10" (Marchese et al., *Genomics* 29:335–344 (1995)), "hGR3" (Hinuma et al., Nature 393:272–276 (1998)) or "UHR-1" (Welch et al., *Biochem. Biophys. Res. Commun.* 209:606–613 (1995)). A "PrRP receptor" can have minor modifications to the native mammalian sequence, so long as the minor modifications do not significantly alter its ability to bind PrRP, interact with AMPA receptor associated molecules, signal through a G-protein coupled signal transduction pathway, or modulate AMPA receptor signaling, depending on the particular application of the PrRP receptor in the methods of the invention.

The PrRP receptor to be contacted in the methods of the invention can be naturally expressed in a tissue, cell or extract. Alternatively, where it is desired to increase the PrRP receptor concentration, or to express PrRP receptor in host cells where it is not normally expressed, including mammalian, yeast and bacterial cells, the PrRP receptor can be recombinantly expressed. Methods of recombinantly expressing PrRP receptor, either transiently or stably, in a variety of host cells, are well known in the art (see, for example, Hinuma et al., *Nature* 393:272–276 (1998) and Roland et al., *Endocrinology* 140:5736–5745 (1999)).

As used herein, the term "predetermined signal" refers to a readout, detectable by any analytical means, that is a qualitative or quantitative indication of activation of G-protein-dependent signal transduction through PrRP receptor. The term "G-protein" refers to a class of heterotrimeric GPT binding proteins, with subunits designated G$\alpha$, G$\beta$ and G$\gamma$, that couple to seven-transmembrane cell surface receptors to transduce a variety of extracellular stimuli, including light, neurotransmitters, hormones and odorants to various intracellular effector proteins. G proteins are present in both eukaryotic and prokaryotic organisms, including mammals, other vertebrates, Drosophila and yeast.

As described in Hinuma et al., *Nature* 393:272–276 (1998), contacting PrRP receptor with PrRP leads to activation of arachidonic acid metabolite release in mammalian cells recombinantly expressing PrRP receptor. Therefore, an exemplary predetermined signal that is a qualitative or quantitative indication of activation of G protein-dependent signal transduction through PrRP receptor is arachadonic acid metabolite release. Similarly, as described in Roland et al., *Endocrinology* 140:5736–5745 (1999), contacting PrRP receptor with PrRP leads to calcium mobilization in mammalian cells recombinantly expressing PrRP receptor, which can be measured, for example, using the calcium indicator fluo-3 and a fluorescence monitoring system.

If desired, a predetermined signal other than arachadonic acid metabolite release or $Ca^{2+}$ influx can be used as the readout in the methods of the invention. The specificity of a G-protein for cell-surface receptors is determined by the C-terminal five amino acids of the G$\alpha$ subunit. The nucleotide sequences and signal transduction pathways of different classes and subclasses of G$\alpha$ subunits in a variety of eukaryotic and prokaryotic organisms are well known in the art. Thus, any convenient G-protein mediated signal transduction pathway can be assayed by preparing a chimeric G$\alpha$ containing the C-terminal residues of a G$\alpha$ that couples to PrRP receptor, such as G$\alpha$q, with the remainder of the protein corresponding to a G$\alpha$ that couples to the signal transduction pathway it is desired to assay.

Methods of recombinantly expressing chimeric G$\alpha$ proteins, and their use in G-protein signaling assays, are known in the art and are described, for example, in, and Saito et al., *Nature* 400:265–269 (1999), and Coward et al., *Anal. Biochem.* 270:2424–248 (1999)).

Signaling through G proteins can lead to increased or decreased production or liberation of second messengers, including, for example, arachidonic acid, acetylcholine, diacylglycerol, cGMP, cAMP, inositol phosphate and ions; altered cell membrane potential; GPT hydrolysis; influx or efflux of amino acids; increased or decreased phosphorylation of intracellular proteins; or activation of transcription. Thus, by using a chimeric G$\alpha$ subunit that binds PrRP receptor and couples to a desired signal transduction pathway in the methods of the invention, those skilled in the art can assay any convenient G-protein mediated predetermined signal in response to a PrRP receptor agonist or antagonist.

Various assays, including high throughput automated screening assays, to identify alterations in G-protein coupled signal transduction pathways are well known in the art. Various screening assay that measure $Ca^{++}$, cAMP, voltage changes and gene expression are reviewed, for example, in Gonzalez et al., *Curr. Opin. in Biotech.* 9:624–631 (1998); Jayawickreme et al., *Curr. Opin. Biotech.* 8:629–634 (1997); and Coward et al., *Anal. Biochem.* 270:2424–248 (1999). Yeast cell-based bioassays for high-throughput screening of drug targets for G-protein coupled receptors are described, for example, in Pausch, *Trends in Biotech.* 15:487–494 (1997). A variety of cell-based expression systems, including bacterial, yeast, baculovirus/insect systems and mammalian cells, useful for detecting G-protein coupled receptor agonists and antagonists are reviewed, for example, in Tate et al., *Trends in Biotech.* 14:426–430 (1996).

Assays to detect and measure G-protein-coupled signal transduction can involve first contacting the isolated cell or membrane with a detectable indicator. A detectable indicator can be any molecule that exhibits a detectable difference in a physical or chemical property in the presence of the substance being measured, such as a color change. Calcium indicators, pH indicators, and metal ion indicators, and assays for using these indicators to detect and measure selected signal transduction pathways are described, for example, in Haugland, *Molecular Probes Handbook of Fluorescent Probes and Research Chemicals*, Sets 20–23 and 25 (1992–94). For example, calcium indicators and their use are well known in the art, and include compounds like Fluo-3 AM, Fura-2, Indo-1, FURA RED, CALCIUM GREEN, CALCIUM ORANGE, CALCIUM CRIMSON, BTC, OREGON GREEN BAPTA, which are available from Molecular Probes, Inc., Eugene Oreg., and described, for example, in U.S. Pat. Nos. 5,453,517, 5,501,980 and 4,849,362.

Assays to determine changes in gene expression in response to a PrRP receptor agonist or antagonist can involve first transducing cells with a promoter-reporter nucleic acid construct such that a protein such as β-lactamase, luciferase, green fluorescent protein or β-galactosidase will be expressed in response to contacting PrRP receptor with a PrRP receptor agonist or antagonist. Such assays and reporter systems are well known in the art.

An assay to determine whether a candidate compound is a PrRP receptor agonist or antagonist, is performed under conditions in which contacting the receptor with a known PrRP agonist, such as a PrRP, including PrRP-31 or PrRP-20, would produce a predetermined signal. If desired, the assay can be performed in the presence of a known PrRP agonist, such as a PrRP. Preferably, the PrRP concentration will be within 10-fold of the $EC_{50}$. Thus, an agonist that competes with PrRP for signaling through the PrRP receptor, or indirectly potentiates the signaling activity of PrRP, can be readily identified. Likewise, an antagonist that prevents PrRP from binding the PrRP receptor, or indirectly decreases the signaling activity of PrRP, can also be identified.

As described in Example II, below, functional interaction of PrRP with GPR10 results in the association of GPR10 through its C-terminus with AMPA receptor associated molecules. Thus, a further signaling assay for identifying a PrRP agonist or antagonist consists of contacting a PrRP receptor with a candidate compound under conditions wherein PrRP promotes interaction of PrRP receptor with an AMPA receptor associated protein, and determining the ability of the candidate compound to promote the interaction of the PrRP receptor with the AMPA receptor associated protein. A candidate compound that promotes the interaction of PrRP receptor with an AMPA receptor associated protein is characterized as a PrRP receptor agonist. In contrast, a candidate compound that reduces the interaction of PrRP receptor with an AMPA receptor associated protein is characterized as a PrRP receptor antagonist.

Exemplary AMPA receptor associated molecules include PICK1 (see Xia et al., Neuron 22:179–187 (1999)), GRIP1 (Dong et al., *J. Neurosci.* 19:6930–6941 (1999)), and GRIP2/ABP (Dong et al., *J. Neurosci.* 19:6930–6941 (1999); Srivista et al., Neuron 21:581–591 (1998)), which are PDZ domain containing proteins, and other proteins that similarly interact with the GluR2 or GluR3 subunits of AMPA receptors.

Methods of determining the interaction between PrRP receptor and an AMPA receptor associated protein, and suitable compositions for practicing the methods, are described in Example II, below. For example, a cell, such as a mammalian, yeast or bacterial cell, can be cotransfected with a nucleic acid expression construct directing the expression of PrRP receptor, and a nucleic acid molecule expression construct directing the expression of AMPA receptor associated protein, and the cell contacted with a candidate compound. Interaction between the PrRP receptor and AMPA receptor associated protein following such contacting can be determined, for example, by co-immunoprecipitation of the two proteins, or by intracellular or surface clustering of the two proteins. Nucleic acid expression constructs and suitable host cells for expressing PrRP receptor and AMPA receptor associated proteins, and immunological reagents and methods suitable for detecting such interactions, are known in the art.

A candidate compound can alternatively or additionally be assayed to determine whether it is a PrRP receptor agonist or antagonist by a PrRP receptor binding assay. If desired, a binding assay can be followed by a signaling assay, to determine whether the identified compound is a PrRP receptor agonist or antagonist. Receptor binding assays, including high-throughput automated binding assays, are well known in the art, and any suitable direct or competitive binding assay can be used. Exemplary high-throughput receptor binding assays are described, for example, in Mellentin-Micelotti et al., *Anal. Biochem.* 272: P182–190 (1999); Zuck et al., *Proc. Natl. Acad. Sci.* USA 96:11122–11127 (1999); and Zhang et al., *Anal. Biochem.* 268;134–142 (1999). The assay format can employ a cell, cell membrane, or artificial membrane system, so long as the PrRP receptor is in a suitable conformation for binding PrRP with a similarly affinity and specificity as a PrRP receptor expressed on the surface of a mammalian cell.

Contemplated binding assays can involve detectably labeling a candidate compound, or competing an unlabeled candidate compound with a detectably labeled PrRP agonist, such as a PrRP. A detectable label can be, for example, a radioisotope, fluorochrome, ferromagnetic substance, or luminescent substance. Exemplary radiolabels useful for labeling compounds include $^{125}$I, $^{14}$C and $^{3}$H. Methods of detectably labeling organic molecules, either by incorporating labeled amino acids into the compound during synthesis, or by derivatizing the compound after synthesis, are known in the art.

In the binding and signaling assays described above, appropriate conditions for determining whether a compound is a PrRP agonist or antagonist are those in which a control PrRP exhibits the binding or signaling property. The control assay can be performed before, after or simultaneously with the test assay.

The invention also provides methods of identifying compounds that modulate AMPA receptor signaling, including compounds that suppress AMPA receptor signaling and compounds that enhance AMPA receptor signaling. Such compounds can be used, for example, as therapeutic compounds for controlling absence seizures, promoting wakefulness, and promoting sleep, as well as in the prevention and treatment of conditions associated with tissues in which GPR10 is expressed. Such compounds can also be used, for example, in the design and development of compounds which themselves can be used as therapeutics, or for further analysis of biochemical pathways.

The method consists of providing one or more compounds that are PrRP receptor agonists or antagonists and determining the ability of the compound to modulate AMPA receptor signaling. The one or more compounds that are PrRP receptor agonists or antagonists can be identified, isolated or prepared by the methods and criteria set forth above.

Assays for determining AMPA receptor signaling can either directly measure AMPA receptor electrophysiological activity in a cell or tissue, or measure a biochemical or physiological property that is correlated with AMPA receptor activity. Appropriate assays and conditions for determining whether a compound modulates AMPA receptor signaling are those in which a control PrRP modulates AMPA receptor signaling. The control assay can be performed before, after or simultaneously with the test assay, depending on the particular assay. Such assays are known in the art or described herein, and include both manual and high-throughput automated assays.

A method of determining whether a PrRP receptor agonist or antagonist modulates AMPA receptor electrophysiological activity can involve determining AMPA receptor-mediated oscillatory activity in a tissue, such as a neural tissue, that expresses both PrRP receptors and AMPA receptors. Example III, below, describes exemplary conditions for determining AMPA receptor-driven oscillatory activity in a thalamic preparation. Application of PrRP reduced AMPA receptor mediated oscillatory activity, in a dose-dependent manner. Accordingly, an assay of thalamic oscillatory activity can be used to determine whether a compound modulates AMPA receptor signaling.

A further method of determining whether a PrRP receptor agonist or antagonist modulates AMPA receptor electrophysiological activity can involve an assay of the electrophysiological properties of a single cell or cell population which normally expresses (e.g. RTN neurons), or which recombinantly expresses, functional PrRP receptors and AMPA receptors. Methods of transiently or stably transfecting cells with AMPA receptors are well known in the art and are described, for example, in Hall et al., *J. Neurochem.* 68:625–630 (1997), and in Hennegriff et al., *J. Neurochem.* 68:2424–2434 (1997).

Example VI, below, and Smith et al., *J. Neuroscience* 20:2073–2085 (2000), describe exemplary conditions for determining AMPA receptor mediated electrophysiological recordings from whole cells. In brief, the method involves detecting AMPA receptor mediated currents using whole cell patch clamp recordings in the presence of an AMPA agonist. The modulatory effect of a test compound on the AMPA receptor mediated currents can thus be determined. Such assays can be performed in the presence of a drug such as cyclothiazide to reduce AMPA receptor densensitization.

Alternatively, or additionally, a method of determining whether a PrRP agonist or antagonist modulates AMPA receptor signaling activity can involve an assay of AMPA receptor-mediated second messenger responses in cells expressing functional PrRP receptors and AMPA receptors. Such assays are advantageous in that they are readily amenable to automation, using methods known in the art, allowing rapid and high-throughput screening of compounds.

Example VI, below, describes exemplary conditions for determining AMPA receptor mediated calcium ion or sodium ion influx into cells in response to a compound that modulates AMPA receptor signaling. In brief, the method involves detecting AMPA receptor mediated ion influx using fluorescent ion indicators and either microscopic visualization, or an automated fluorometric imaging plate reader (FLIPR). The modulatory effect of a test compound on AMPA receptor mediated ion influx can thus be determined.

The invention also provides methods of identifying compounds for controlling absence seizures. The method consists of providing a compound that is a PrRP agonist, and determining the ability of the compound to control absence seizures in a mammal. Optionally, the compound can be a compound determined to suppress AMPA receptor mediated signaling by any of the assays described herein.

Assays for determining whether a compound controls absence seizures in a mammal are known in the art. For example, as described in Example IV, below, absence seizure activity can be determined in a mammalian model of absence epilepsy, the GAERS, in which spontaneous spike-and-wake discharges are evidenced by EEG recordings. Administration of PrRP decreased seizure activity in the GAERS, in a dose-dependent manner. Accordingly, an in vivo assay in a mammal susceptible to absence seizures, including a rodent, non-human primate, or human, can be used to identify a compound for controlling absence seizures.

Example VII, below, describes exemplary conditions for determining the ability of a PrRP receptor agonist to promote wakefulness in mammals. In brief, the methods involve obtaining EEG and EMG patterns and observing behavioral properties correlated with mammalian wakefulness or sleep, such as activity. An EEG pattern characterized by high amplitude waves associated with deep sleep was observed prior to PrRP treatment. Upon PrRP treatment, this EEG pattern was altered to an EEG pattern characterized by lower amplitude waves associated with increased wakefulness. The silent EMG pattern observed prior to PrRP treatment was characteristic of REM sleep, while the EMG pattern observed upon PrRP treatment was characteristic of increased wakefulness. The effect of a PrRP receptor agonist or antagonist on a wakefulness or sleep state of a mammal can thus be determined using the experimental system described in Example VII.

The invention further provides methods of screening for compounds for promoting wakefulness. The method consists of providing a compound that is a PrRP receptor agonist and determining the ability of the compound to promote wakefulness in a mammal. Optionally, the compound can be a compound determined to suppress AMPA receptor mediated signaling in any of the assays described herein.

In addition, the invention provides methods of screening for compounds for promoting sleep. The method consists of providing a compound that is a PrRP receptor antagonist and determining the ability of the compound to promote sleep in a mammal.

Assays for determining whether a compound promotes wakefulness or sleep in a mammal are known in the art. For example, as described in Example VII, below, wakefulness and sleep can be determined in a strain of normal rat. Administration of PrRP increased wakefulness, as evidenced by cortical EEG (ECoG), EMG and wake time measurements, in a dose-dependent manner. Accordingly, an in vivo assay in any mammal, including a rodent, canine, horse, non-human primate, or human, can be used to identify a compound for promoting wakefulness or sleep.

A candidate compound can be tested for its effects on one or more behavioral and physiological properties correlated with mammalian sleep or wake states. Behavioral properties correlated with mammalian sleep or wake states include, for example, activity, sleep latency, and arousal threshold. Activity includes all behavioral activities normally exhibited by a mammal, such as movement, grooming, eating and the like. In humans, an exemplary activity that can be useful for determining quality of sleep is major body repositioning, which can be assessed as rate of major body position changes per hour. Activity can be evaluated throughout a normal wake period or throughout a normal sleep period, or both, or evaluated for only part of a normal wake or sleep period, such as for at least 10 minutes, 30 minutes, 1, 2, 4, 6, 8 or 12 hours. Once activity during a normal sleep period or normal wake period is established, those skilled in the art can readily evaluate whether a candidate compund increases or decreases intensity of activity or alters the pattern of activity during all or part of that period.

For certain applications, it will be preferable to evaluate activity following sleep deprivation. For example, a compound that promotes wakefulness or sleep can be examined in a sleep-deprived mammal. Sleep deprivation is generally performed for a sufficient period of time during a normal sleep period to result in a detectable decrease in activity, increase in sleep or increase in intensity of sleep during the subsequent period, also known as a rebound effect. Any method appropriate for the particular mammal can be used to deprive an animal of sleep. In certain mammals, such as humans, it can be preferable to cause sleep-deprivation by using noise or other stimulation for short or long periods. In particular, slow wave sleep can be reduced or interrupted by stimulating a mammal when EEG or other measurements indicate the beginning of a slow wave sleep stage.

Various manual and automated methods can be used to evaluate intensity and patterns of activity. For example, activity can be detected visually, either by direct observation, by time lapse photography and by use of an activity detector, such as an actigraph, which can be conveniently used to detect movement and nonmovement in humans. For humans, sleep logs, diaries, self-administered questionnaires and symptom checklists can be useful for determining activity and sleep quality and quantity.

Another behavioral property correlated with mammalian sleep or wake states is sleep latency, which refers to the number of minutes before the onset of a measurable sleep cycle. Once normal latency to sleep, with or without sleep deprivation, is established for a particular mammal, one skilled in the art can evaluate whether a candidate compound increases or decreases this property. A further behavioral property useful for assessing human wake and sleep states is sleep efficiency, which is the percentage of time spent in bed versus the time spent asleep. Once normal sleep efficiency, with or without sleep deprivation, is established for a particular individual, one skilled in the art can evaluate whether a candidate compound increases or decreases this property.

Arousal threshold refers to the amount of stimulation required to elicit a behavioral response. Any reproducible stimulus can be used to evaluate arousal threshold, for example, vibratory stimulus, noise, electrical stimulation, heat, light and the like. Arousal threshold can be assessed by determining activity, such as by determining the number per hour of measurable, but brief, changes during sleep to waking brain wave activity. Mammals that are in a state of wakefulness will exhibit a behavioral response at a lower level of stimulation than mammals that are in a sleep state. Further, an animal that is deeply asleep will exhibit an increased arousal threshold compared to an animal that is less deeply asleep. Therefore, arousal threshold is a measurement of sleep versus wakefulness, as well as intensity of sleep. Once normal arousal threshold associated with sleep and wakefulness are established for a particular mammal, those skilled in the art can readily evaluate whether a candidate compound increases or decreases this property.

Physiological properties correlated with mammalian sleep or wake states include frequency, amplitude and type of electrophysiological signals, heart rate, muscle tone, eye movement and the like. Electrophysiological measurements can be used to determine a stage of sleep experienced by a mammal, as well as the duration of a stage of sleep, and a change in sleep stage. Sleep stages are variations in states of consciousness and include, for example, light sleep, deeper sleep, such as slow wave sleep, and REM sleep. Correlative electrophysiological measurements characteristic of such sleep stages are well known to those skilled in the art.

Use of electrophysiological methods for determining sleep stage and correlation of various phases and states of sleep and arousal are described, for example, in Timo-Iaria et al., *Physiology and Behavior*, 5:1057–1062, (1970) and Vanderwolf et al. *The Behavioral and Brain Sciences*, 4:459–514 (1981). Brain wave activity associated with sleep or wakefulness can be determined, for example, by electroencephalogram (EEG) measurement. In particular, forebrain electroencephalograph activity amplitude or frequency patterns can be used to determine a state of wakefulness or sleep in a mammal, including a human. For example, during non-rapid eye movement (non-REM) sleep, cortical EEG (ECoG) exhibits predominant large amplitude, slow-wave activity (<1 Hz) while low-amplitude, high-frequency fluctuations are typically observed during most periods of alert waking and REM sleep. Light sleep can be characterized by EEG wave patterns termed sleep spindles, which are increases in wave frequency, and K complexes, which are increases in wave amplitude. In contrast, deep sleep can be characterized by EEG wave patterns containing slow, high amplitude brain waves. Therefore, electrophysiological measurements, such as EEG measurement, in particular ECoG measurement, can be used to determine a state of wakefulness or sleep in a mammal.

REM sleep, which is characterized by sudden and substantial loss in muscle tone and an increase in rapid eye movement, can be distinguished from other sleep stages using various electrophysiological measurements. For example, REM sleep can be distinguished from other stages of sleep by measurement of muscle tone by electromyography (EMG) and measurement of eye movement by electrooculogram (EOG). Example VII describes the use of EMG from dorsal neck muscles to monitor sleep in rats. Methods of using EMG for monitoring sleep in individuals, such as chin EMG, as well as EOG, are well known to those skilled in the art. Therefore, the effect of a compound that promotes wakefulness or sleep on specific stages of sleep, such as an increase or decrease in slow wave sleep or REM sleep, can be determined. A combination of two or more electrophysiological measurements can be used to determine a sleep stage, duration of sleep stage or change in sleep stage in a mammal.

Methods for evaluating sleep in a mammal are useful for both diagnosing a variety of sleep disorders to determine if an individual is a candidate for treatment with a PrRP receptor agonist or antagonist, as well as to evaluate an individual's response to administration of a PrRP receptor agonist or antagonist. Methods for evaluating sleep can involve continuous and simultaneous monitoring of various behavioral and physiological parameters of sleep. Such sleep evaluations include nighttime sleep studies, such as a polysomnogram, and daytime sleep studies, such as a Multiple Sleep Latency Test. Such sleep studies can be used to assess the quality and quantity of sleep by determining types of sleep stages experienced, duration of sleep, arousal threshold, sleep latency, activity, and other measurements, if desired. A sleep study can include, for example, electrophysiologic methods, such as measurements from an electroencephalogram (EEG), electro-oculogram (EOG) or electromyogram (EMG). In addition to these electrophysiologic methods, other measurements and conditions of a mammal can be monitored, for example, electrocardiogram (ECG), airflow, ventilation and respiratory effort, transcutaneous monitoring or end tidal gas analysis, extremity muscle activity, motor activity movement, gastroesophageal reflux, continuous blood pressure monitoring, snoring, body positions, amount of REM sleep, determination of the latency to the first REM episode, and the like. Those skilled in the art will know how to review, interpret and report the findings of such monitoring.

Following administrating of a candidate compound to a mammal, wake time, EEG and EMG measurements and any of the behavior or physiological properties correlated with mammalian wake or sleep states described above can be evaluated, and a determination made as to whether the compound alters, such as increases or decreases, the measurement or property compared to a baseline or established value for the measurement or property in an untreated control.

Additionally, a candidate compound can be tested for its effects on one or more additional behavioral or physiological properties in order to determine its most effective application in therapy. For example, it may be desirable to determine whether a compound that promotes wakefulness does so without significantly altering sleep latency when the effect of the compound wears off. It may also be desirable to determine whether the compound that promotes wakefulness does so without a compensatory sleep rebound effect. It can be further be desirable to determine whether the compound that promotes wakefulness effects other physiological or psychological properties or behaviors such as locomotor activity, anxiety, blood pressure and heart rate.

The methods of the invention for screening for a compound for promoting wakefulness are useful for identifying a PrRP receptor agonist that promotes wakefulness. Therefore, the invention provides a method of promoting wakefulness in an animal by administering to the mammal an effective amount of a PrRP receptor agonist.

An amount of a PrRP agonist effective to promote wakefulness is an amount effective to reduce a determined parameter (for example, amount of sleep, sleepiness, tendency to fall asleep, slow wave sleep) or increase a determined parameter (for example, wake time, sleep latency, activity) by at least 10%. Preferably, the determined parameter will be reduced by at least 20%, more preferably at least 50%, such as at least 80%, in at least some treated mammals. Accordingly, a treatment that promotes wakefulness will be useful in improving the quality of life or obtaining the desired level of wakefulness in the treated mammals. Further description of effective amounts, formulations and routes of administration of PrRP agonists useful in the methods of the invention is provided below.

The methods of the invention for screening for a compound for promoting sleep are useful for identifying a PrRP receptor antagonist that promotes sleep. Therefore, the invention provides a method of promoting sleep in an animal. The method consists of administering to the mammal an effective amount of a PrRP receptor antagonist.

An amount of a PrRP antagonist effective to promote sleep is an amount effective to increase the determined parameter (for example, sleep, sleepiness, tendency to fall asleep, slow wave sleep, arousal threshold) or decrease the determined parameter (for example, wake time, activity, sleep latency) by at least 10%. Preferably, the determined parameter will be reduced by at least 20%, more preferably at least 50%, such as at least 80%, in at least some treated mammals. Accordingly, a treatment that promotes sleep will be useful in improving the quality of life in the treated mammals. Further description of effective amounts, formulations and routes of administration of the PrRP antagonists useful in the methods of the invention is provided below.

It is expected that the PrRP receptor agonists will have beneficial activities apart from, or in addition to, controlling absence seizures and promoting wakefulness. It is similarly expected that the PrRP receptor antagonists will have beneficial activities apart from, or in addition to, promoting sleep. As described herein, high levels of GPR10 expression have been observed in a number of discrete locations in the brain and peripheral tissues (see Example I and Table 2). In particular, GPR10 is expressed at high levels in the GABAergic neurons of the RTN. The GABAergic neurons of the RTN change their firing patterns in response to sleep and wake states. During periods of EEG-synchronized, deep sleep, RTN neurons generate rhythmic, high-frequency bursts of action potentials, while during waking and REM sleep, these neurons generate sequences of tonic action potential activity (for a review, see McCormick et al., *Annu. Rev. Neurosci.*, 20:185–215 (1997)). GPR10 is expressed in other areas of the brain known to be involved in regulating sleep and attention, for example, preoptic and hypothalamic areas of the brain, such as the tuberomammillary nucleus, as well as in the locus coeruleus. Accordingly, it is contemplated that PrRP receptor agonist and antagonists, will be effective in preventing or ameliorating sleep disorders and attention disorders by modulating signaling through the GABAergic neurons of the RTN. Attention disorders are well known in the art and include, for example, attention deficit hyperactivity disorder, affective disorders, and disorders of memory.

A variety of sleep disorders are also well known in the art and are described, for example, in Diagnostic and Statistical Manual of Mental Disorders, 4th Edition (1994), published by the American Psychiatric Association. The most common sleep disorder is primary insomnia, or a difficulty in initiating or maintaining sleep, which affects a large percentage of the population at some point in their lives. Other common sleep disorders include hypersomnia, or excessive daytime sleepiness, narcolepsy, which is characterized by sudden and irresistible bouts of sleep, and sleep apnea, which is a temporary cessation of breathing during sleep.

As described herein, GPR10 is also expressed in the Area Postrema (AP), Bed nucleus stria terminalis (BST), Central nucleus amygdala (CeA), parabrachial nucleus (PB), dorsal raphe, caudal (DRC), hypothalamic nucleus (Hypo), hypothalamic paraventricular nucleus (PVN), locus coeruleus (LC), lateral hypothalamus nucleus (LH), lateral preoptic nucleus (LPO), median preoptic nucleus (MnPO), MPA (medial preoptic area), MPO (medial preoptic nucleus), nucleus of the solitary tract (NTS), periventricular nucleus (Pe), suprachiasmatic nucleus (Sch), supraoptic nucleus (SO), Superior colliculus (SC), and Shell, nucleus accumbens (SNAc), dorsomedial hypothalamic nucleus (DMH), ventromedial hypothalamus (VMH), ventral tuberomamillary nucleus (VTM), ventromedial preoptic nucleus (VMPO) of the brain, as well as in peripheral tissues including the Adrenal medulla (AdM), uterus. Accordingly, it is contemplated that PrRP receptor agonists and antagonists will be effective in preventing, ameliorating or modulating conditions associated with these regions of the brain and periphery, including those shown in Table 1, below.

TABLE 1

Therapeutic Potential of PrRP

| Therapeutic Potential | GPR10 Localization |
|---|---|
| Bulimia | LH, VLH, VMH, DMH, Arc, SNAc, NTS, AP |
| Anorexia | LH, VLH, VMH, DMH, Arc, SNAc, NTS, AP |
| Obesity | LH, VLH, VMH, DMH, Arc, SNAc, NTS, AP |
| Chronic pain states | PB, NTS |
| Stress-induced anorexia | Hypo, BST, CeA |
| Stress-induced hypertensive crisis | Lateral septum, BST, CeA, PVN, LC, SNAc |
| Anxiety | Lateral septum, BST, CeA, PVN, LC, SNAc |
| Excessive fear response | Lateral septum, BST, CeA, PVN, LC, SNAc |
| Excessive stress | Lateral septum, BST, CeA, PVN, LC, SNAc |
| Posttraumatic Stress disorder | BST, CeA, Hypo, AP |
| Nicotine induced cardiac arrhythmias | NTS, AP |
| Nicotine induced coronary spasms | NTS, AP |
| Pheochromocytoma | AdM |
| Insomnia | RTN, MnPO, MPA, VMPO, LPO, VTM, LC, DRC, SCh |
| Hypersomnia syndrome | RTN, MnPO, MPA, VMPO, LPO, VTM, LC, DRC, SCh |
| Narcolepsy | RTN, MnPO, MPA, VMPO, LPO, VTM, LC, DRC, SCh |
| Excessive somnolence (need for alertness) | RTN, MnPO, MPA, VMPO, LPO, VTM, LC, DRC, Sch |
| Petit mal (absence) seizure | RTN |
| Visual processing and attention deficits | SC |
| Drug addiction | SNAc |
| Inducing labor | Uterus |
| Birth control | Uterus |
| Sexual dysfunction | MPO, VMH |
| Decreased libido | MPO, VMH |
| Sex hormone dysregulation (for example, leutinizing hormone, follicle stimulating hormone dysregulation) | MPO, VMH |
| Misregulated release of prolactin | PVN |
| Misregulated release of oxytocin/vasopressin | SO, PVN |
| Misregulated release of leutinizing hormone, follicle stimulating hormone | MPO |
| Misregulated release of somatostatin | Pe |
| Hypertension | AP, NTS, PVN, DMH, BST, CeA |
| Hypotension | AP, NTS, PVN, DMH, BST, CeA |
| Fluid imbalance | AP, NTS, PVN, DMH, BST, CeA |

It is known in the art that currently available drugs for controlling absence seizures are effective in the prevention and treatment of a variety of neurologic and psychiatric conditions. For example, valproate, one of the most commonly used medications for controlling absence seizures, is also useful in the treatment of bipolar and schizoaffective disorders, depression, anxiety, alcohol withdrawal and dependence, agitation associated with dementia, impulsive aggression, neuropathic pain, and for the prophylactic treatment of migraine (see, for example, Loscher, *Prog. Neuro-biol.* 58:31–59 (1999), and Davis et al., *J. Clin. Psychopharmacol.* 20:1S-17S (2000)). Thus, PrRP receptor agonists and antagonists can be used to treat conditions in which other anti-absence seizures drugs are effective.

The PrRP agonists and antagonists of the invention can be formulated and administered by those skilled in the art in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for controlling absence seizures in humans can be extrapolated based on the activity of the compound in the assays described herein. Similarly, an appropriate amount and formulation for promoting wakefulness or sleep in humans can be extrapolated based on the activity of the compound in the assays described herein. An appropriate amount and formulation for use in humans for other indications can be extrapolated from credible animal models known in the art of the particular disorder.

The total amount of compound can be administered as a single dose or by infusion over a relatively short period of time, or can be administered in multiple doses administered over a more prolonged period of time. Additionally, the compounds can be administered in slow-release matrices, which can be implanted for systemic delivery or at the site of the target tissue. Contemplated matrices useful for controlled release of therapeutic compounds are well known in the art, and include materials such as DepoFoam™, biopolymers, micropumps, and the like.

The compounds and compositions of the invention can be administered to the subject by any number of routes known in the art including, for example, intravenously, intramuscularly, subcutaneously, intraorbitally, intracapsularly, intraperitoneally, intracisternally, intra-articularly, intracerebrally, orally, intravaginally, rectally, topically, intranasally, or transdermally. A preferred route for humans is oral administration.

A PrRP receptor agonist or antagonist can be administered to a subject as a pharmaceutical composition comprising the compound and a pharmaceutically acceptable carrier. Those skilled in the art understand that the choice of a pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters.

A pharmaceutically acceptable carrier can contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins.

For applications that require the compounds and compositions to cross the blood-brain barrier, formulations that increase the lipophilicity of the compound are particularly desirable. For example, a PrRP receptor agonist or antagonist can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

A PrRP receptor agonist or antagonist can also be prepared as nanoparticles. Adsorbing peptide compounds onto the surface of nanoparticles has proven effective in delivering peptide drugs to the brain (see Kreuter et al., *Brain Res.* 674:171–174 (1995)). Exemplary nanoparticles are colloidal polymer particles of poly-butylcyanoacrylate with PrRP adsorbed onto the surface and then coated with polysorbate 80.

In current absence seizure treatment regimes, more than one compound is often administered to an individual for maximal seizure control. Thus, for use in controlling absence seizures, a PrRP receptor agonist can advantageously be formulated with a second compound that controls absence seizures. Such compounds include, for example, valproate, ethosuximade, flunarizine, trimethadione and lamotrigine. Contemplated methods of controlling absence seizures include administering the compounds and compositions of the invention alone, in combination with, or in sequence with, such other compounds.

Similarly, in current sleep disorder treatment regimes, more than one compound is often administered to an individual for maximal reduction in symptoms. Thus, for use in promoting wakefulness or sleep, a PrRP receptor agonist or antagonist can be formulated with a second compound that promotes wakefulness or sleep. Compounds that promote wakefulness include, for example, amphetamine, methylphenidate, ephedrine, cathinone and caffeine. Sleep attacks associated with narcolepsy generally respond to stimulants such as methylphenidate (Ritalin), modafinil, and amphetamines such as dextroamphetamine, mazindol and selegiline. Therefore, a PrRP receptor agonist can be combined with such compounds to effectively promote wakefulness in individuals having narcolepsy., Well known compounds that promote sleep include, for example, opiates, barbiturates, benzodiazepines, and anesthetics. A PrRP receptor antagonist that induces sleep can be combined with such compounds to effectively promote sleep, or can be used to increase the efficacy of sleep-promoting compounds, thereby reducing the required dosage of compounds that are addictive or have unwanted side-effects.

In addition, a PrRP receptor agonist or antagonist can be formulated with a compound that reduces a symptom associated with the treated disorder. For example, a combination of a PrRP receptor agonist can be combined with a compound effective for reducing cateplexy, such as a dopamine receptor D2/D3 antagonist, to provide a composition useful for treating narcolepsy. Contemplated methods of promoting wakefulness or sleep include administering the compounds and compositions of the invention and PrRP receptor agonists and antagonists alone, in combination with, or in sequence with, such other compounds.

The following examples are intended to illustrate but not limit the present invention.

EXAMPLE I

Localization of GPR10 in the Rat Brain

This example shows the distribution of GPR10 mRNA in the brain, and particularly shows that GPR10 is highly expressed the GABAergic neurons of the RTN.

Previous studies using Northern blot analysis have demonstrated that the receptor for PrRP, GPR10 is highly expressed in the pituitary, but absent in the brain. In order to determine the expression pattern of GPR10 in the brain, the more sensitive approach of in situ hybridization analysis was used.

In situ hybridization was performed essentially as described in Winzer-Serhan et al., *Brain Res. Brain Res. Protoc.* 3:229–241 (1999), and Winzer-Serhan et al., *J. Comp. Neural.* 386:540–554 (1997). Briefly, adult Sprague-Dawley rat brains were quickly removed and placed in methylbutane cooled to −20° C. for 1 minute. Twenty micron frozen sections were thaw-mounted onto poly-L-lysine coated glass slides, fixed in 4% paraformaldehyde in 0.1 M PBS pH 7.4, dessicated and stored at −20° C. until prehybridization. Pretreated sections were incubated overnight at 60° C. in hybridization buffer (50% formamide, 10% dextran sulfate, 500 µg/ml tRNA, 10 mM DTT, 0.3 M NaCl, 10 mM Tris pH 8.0, 1 mM EDTA pH 8.0) with $^{35}$S-labeled GPR10 sense and antisense cRNA probes ($10^7$ cpm/ml). Sections were washed, dehydrated in graded ethanol, and opposed to B-max film with $^{14}$C standards of known radioactivity. Slides were dipped in liquid Kodak NT2B emulsion and exposed for 4 weeks at 4° C. Developed sections were cresyl violet stained, coverslipped, and viewed under dark field microscopy. Adjacent sections were also labeled with S35-labeled sense GPR10 cRNA as control. The control sections showed no specific staining.

By in situ hybridization analysis, GPR10 was shown to be prominently expressed several discrete locations of the forebrain, midbrain and brainstem, as shown in FIGS. 1A and 1B and Table 2. In situ hybridization analysis of GPR10 expression has also been presented in Roland et al., *Endocrinology* 140:5736–5745 (1999).

The distribution of GPR10 mRNA was examined qualitatively on both autoradiographic images on film as well as under dark field illumination of emulsion dipped sections. Anatomical localization within specific brain nuclei was determined by comparing cresyl violet sections to the rat brain atlas by Paxinos and Watson (*The Rat Brain in Stereotaxic Coordinates*, Academic Press, fourth edition, (1998)). All regions found to have GPR10 expression were only considered specific when they were found to be absent in corresponding sections of the sense probe. In general, sense control sections did not exhibit any substantial staining, except for light staining of the hippocampus and cerebellum, which was also found with similar intensity in the anti-sense sections. These nuclei were therefore determined not to have GPR10 expression, except for the Purkinje cell layer of the cerebellum. To determine relative density of GPR10 expression between nuclei, a preliminary quantitative measure of receptor density was performed using a video-based computerized imaging analysis system (MCID, Imaging Research, St. Catharine's, Ontario, Canada) on nuclei which have good boundaries and are easily circumscribed for density measurements. All measurements were normalized to corresponding regions of the sense control sections. The intensity of GPR10 mRNA was scored in the following manner: + + + + +, very strong expression; + + + +, strong expression; + + +, moderate expression; + +, low expression; +, very low expression or small number of high expressing cells; −, no expression.

The relative postnatal developmental changes were determined quantitatively by measuring the density of each GPR10 expressing nucleus compared to densities of $^{14}$C standards of known radioactivity using a video-based computerized imaging analysis system (MCID, Imaging Research, St. Catharinels, Ontario, Canada). Areas that were too small to be accurate for this type of analysis were examined qualitatively under dark field illumination and compared to the data from the density measurements. The same scoring system used for the adult distribution was also used to determine the postnatal changes in receptor expression.

Brain images were taken from MCID images from film or from emulsion-dipped sections under dark and light-field transillumination microscope (BX50, Olympus, Melville, N.Y.) using the Spot camera (software version 2.2.2, Diagnostic Instruments, Sterling Heights, Mich.). Captured images were imported into and arranged on Adobe Photoshop 5.5 (Adobe, San Jose, Calif.).

Distribution of GPR10 mRNA and GPR10-immunoreactive (GPR10-ir) fibers in adult rat brain were compared. Co-distribution of GPR10 mRNA and GPR10-ir fibers is indicated by the word "Yes," a "*" symbol indicates co-localization in cell bodies, "Ind." indicates that co-localization is indiscernible, and lack of co-localization is indicated by the word "No." Abbreviations in Table 2 are according to Paxinos and Watson, supra, (1999), and are defined herein, in Table 3. GPR10-ir fiber distribution data can be obtained from Ibata et al, *Neurosci. Res.* 38(3):223–30 and Maruyama et al., *Endocrinology* 140(5):2326–33 (1999).

By Northern blot (NB) analysis of a human tissue mRNA blot (obtained from Clontech), GPR10 was also shown to be expressed in the uterus.

TABLE 2

Distribution of GPR10 receptor mRNA and comparison with GPR10-ir fibers

| Region | GPR10 mRNA | GPR10-ir fiber |
|---|---|---|
| Neocortex | | No |
| Frontal | | |
| Layer II | + | |
| Layer III | + | |
| Parietal | | |
| Layer II | + | |
| Layer III | + | |
| Temporal | | |
| Layer II | ++ | |
| Layer III | ++ | |
| Occipital | | |
| Layer II | ++ | |
| Layer III | ++ | |
| Other cortical regions | | No |
| AI | ++ | |
| cc | – | |
| Cg | – | |
| DLO | + | |
| Ent | – | |
| GI | ++ | |
| IL | ++ | |
| LO | + | |
| MO | + | |
| PRL | + | |
| Pir | – | |
| RSA | – | |
| TT | – | |
| VO | + | |
| Telencephalon | | |
| Ventral forebrain | | |
| ac | – | Ind. |
| AcbC | – | Ind. |
| AcbSh | +++ | Ind. |
| HDB | + | Ind. |
| Septum | | Yes |
| LSD | + | |
| LSI | +/– | |
| LSV | + | |
| MS | – | |
| Basal Ganglia | | No |
| Cpu | +/– | |
| Bed Nucleus | | |
| BST1 | +++ | Yes |
| BSTld | +++ | Yes |
| BSTlj | – | Ind. |
| BSTlp | + | Ind. |
| BSTlv | +++ | Yes |
| BSTma | + | Ind. |
| BSTmv | ++ | Yes |
| BSTv | +++ | Yes |
| Amygdala | | |
| BLA | – | Yes |
| CeL | ++ | No |
| CeM | + | No |
| CeC | ++ | No |
| MeAD | + | No |
| MeAV | + | No |
| PMCo | + | No |
| Diencephalon | | |
| Preoptic | | |
| AMPO | +++ | Yes |
| AVPO | +++ | Yes |
| AVPe | ++ | Yes |
| LPO | ++ | Yes |
| MCPO | + | Ind. |
| Superior Colliculus | | No |
| DpG | – | |
| DpWh | – | |
| InG | + | |
| InWh | – | |
| Op | – | |
| SuG | +/– | |
| Cerebellum | | No |
| Cortex | | |
| Molecular | – | |
| Purkinje | +/– | |
| Granule cell | – | |
| Metencephalon | | |
| Bar | – | No |
| DTg | + | Ind. |
| DRC | ++ | Ind. |
| IRT | +/– | No |
| LC | +/– | Yes |
| LPB | | Yes |
| dorsal | ++++ | Ind. |
| external | + | Ind. |
| internal | +++ | Ind. |
| ventral | ++++ | Ind. |
| Me5 | – | No |
| Mo5 | + | No |
| MPB | +++ | Ind. |
| Pr5 | + | No |
| scp | – | No |
| Myelencephalon | | |
| A1 | – | No |
| A2 | + | No |
| AP | ++++ | Yes |
| C1 | – | No |
| C2 | + | No |
| LRt | – | Yes* |
| SolC | ++ | Yes* |
| SolL | + | Yes* |
| SolM | + | Yes* |

TABLE 3

Abbreviations Used in Table 2

| Abbreviation | Definition |
|---|---|
| A1 | A1 noradrenaline cells |
| A2 | A2 noradrenaline cells |
| ac | anterior commissure |
| Acbc | nucleus accumbens, core |
| AcbSh | nucleus accumbens, shell |
| AH | anterior hypothalamic nucleus |
| AI | agranular insular |
| AMPO | anterior medial preoptic nucleus |
| AP | area postrema |
| ArcD | arcuate nucleus, dorsal |
| ArcL | arcuate nucleus, lateral |
| AVPe | anterior ventral periventricular |
| AVPO | anterior ventral preoptic nucleus |
| Bar | Barrington's nucleus |
| BLA | basolateral amygdala |
| BSTl | bed nucleus of stria terminalis, lateral |
| BSTld | bed nucleus of stria terminalis, laterodorsal |
| BSTlj | bed nucleus of stria terminalis, lateral juxtacapsular |
| BSTlp | bed nucleus of stria terminalis, lateral posterior |
| BSTlv | bed nucleus of stria terminalis, lateral ventral |
| BSTma | bed nucleus of stria terminalis, medial anterior |
| BSTmv | bed nucleus of stria terminalis, medial ventral |
| BSTv | bed nucleus of stria terminalis, ventral |
| C1 | C1 adrenaline cells |
| C2 | C2 adrenaline cells |
| cc | corpus callosum |
| CeC | central amygdaloid nucleus, capsular |
| CeL | central amygdaloid nucleus, lateral |
| CeM | central amygdaloid nucleus, medial |
| Cg | cingulate gyrus |
| CIC | central nuc. inf. colliculus |
| CPu | caudate putamen |
| DCIC | dorsal cortex inf. colliculus |
| DLO | dorsolateral orbital cortex |
| DMD | dorsomedial nucleus of hypothalamus |
| DMDC | dorsomedial nucleus, lateral |
| DMDV | dorsomedial nucleus, ventral |
| DpG | deep gray layer, sup. colliculus |
| DpWh | deep white layer, sup. colliculus |
| DRC | dorsal raphe, caudal |
| DTg | dorsal tegmental nucleus |
| ECIC | external cortex inf. colliculus |
| Ent | entorhinal cortex |
| GI | granular insular cortex |
| HDB | horizontal diagonal band of Broca |
| IL | infralimbic cortex |
| InG | intermed. gray layer sup. colliculus |
| InWh | intermed. White layer sup. colliculus |
| IRT | intermed. reticular nucleus |
| LA | lateral anterior hypothalamus |
| LC | locus coeruleus |
| LH | lateral hypothalamus nucleus |
| LO | lateral orbital cortex |
| LPB | lateral parabrachial nucleus |
| LPO | lateral preoptic nucleus |
| LRt | lateral reticular nucleus |
| LSD | lateral septal nucleus, dorsal |
| LSI | lateral septal nucleus, intermediate |
| LSV | lateral septal nucleus, ventral |
| MCPO | magnocellular preoptic nucleus |
| ME | median eminence |
| Me5 | mesehcephalia-5 nucleus |
| MeAD | medial amygdaloid nucleus, anterior dorsal |
| MeAV | medial amygdaloid nucleus, anterior ventral |
| MM | medial mammillary bodies |
| MnPO | median preoptic nucleus |
| MO | medial orbital cortex |
| Mo5 | motor nucleus 5 |
| MPA | medial preoptic area |
| MPB | medial parabrachial nucleus |
| MPO | medial preoptic nucleus |
| MPOC | medial preoptic nucleus, central |
| Op | optic nucleus layer, superior colliculus |
| Pa | paraventricular nucleus |
| PaAM | Pa, anterior magnocellular |
| PaAP | Pa, anterior parvicellular |
| PaLM | Pa, lateral magnocellular |
| PaMP | Pa, medial parvicellular |
| PaPo | Pa, posterior part |
| PaV | Pa, ventral part |
| Pe | periventricular nucleus |
| Pir | piriform cortex |
| PMCo | posteromedial cortical arnygdaloid nucleus |
| PMD | premammillary nucleus, dorsal |
| PMV | premammillary nucleus, ventral |
| Pr5 | principle sensory 5 nucleus |
| PRL | prelimbic cortex |
| PT | paratenial thalamic nucleus |
| RCh | retrochiasmatic area |
| RSA | retrosplenial agranular cortex |
| Rt | reticular thalamic nucleus |
| SCh | suprachiasmatic nucleus |
| scp | superior cerebellar peduncle |
| SO | supraoptic nucleus |
| SolC | nucleus solitary tract nucleus, commissural |
| SolL | nucleus solitary tract nucleus, lateral |
| SolM | nucleus solitary tract nucleus, medial |
| SuG | superficial gray, sup. colliculus |
| TC | tuber cinereum area |
| TT | tenia tecta |
| VLPO | ventrolateral preoptic nucleus |
| VMH | ventromedial hypothalamus |
| VMHDM | VMH, dorsomedial |
| VMHVL | VMH, ventrolateral |
| VO | ventral orbital cortex |
| VTM | ventral tuberomamillary nucleus |
| ZI | zona incerta |

Localization of the RTN plays an important role in the gating of sensory information into the cortex, in generating sleep spindles, a hallmark of slow wave sleep, and is implicated in the formation of absence seizure activity (reviewed in Danober et al., Prog. Neurobiol. 55:27–57 (1998) and McCormick et al., Annu. Rev. Neurosci. 20:185–215 (1997)). The RTN consists of predominantly GABAergic neurons, the activities of which are known to silence thalamocortical activity during spike-wave (absence) seizures, possibly contributing to the loss of consciousness during these states (see Steriade et al., Cereb Cortex 7:583–604 (1997) and Liu et al., Brain Res. 545:1–7 (1991)).

As shown in FIG. 1, in situ double labeling using digoxigenin-GAD and $^{35}$S-GPR10 probes was performed to determine whether GPR10 is expressed on the GABAergic neurons of the RTN. For GAD (glutamic acid decarboxylase) double labeling, the samples were treated as described above, except hybridization included both $^{35}$S labeled GPR10 cRNA and digoxigenin labeled GAD cRNA (E. Jones, University of California, Irvine). Subsequent incubation with alkaline phosphatase conjugated anti-digoxigenin antibody, washes, and substrate development were preformed according to manufacturer's instructions (Genius kit, Roche). Emulsion dipped slides were not cresyl violet stained. Double labeling was detected by viewing GAD positivity with light microscopy and GPR10 labeling under dark field.

The distribution of GPR10 expresssion observed corresponded with the "shell" pattern seen for GAD labeling (see FIGS. 1C and 1D). Examining the labeled sections under higher magnification revealed that GPR10 expression overlaps with the GAD labeling of GABAergic neurons of the RTN (see FIGS. 1E and 1F).

Based on expression of GPR10 in the GABAergic neurons of the RTN, it was predicted that PrRP modulates GABAergic output in the RTN.

EXAMPLE II

Interaction of GPR10 with AMPA Receptor-Interacting Proteins

This example shows that GPR10 interacts with GRIP-like proteins through its cytoplasmic tail, and forms clusters with PICK1.

An analysis of GPR10 sequence revealed that its carboxy-terminal tail contained a sequence motif of 4 amino acids (-SVVI) (SEQ ID NO:24) similar to those found in GluR2 and GluR3 subunits of AMPA receptors (FIG. 2A). The sequence -SVXI (X=any amino acid) has been shown to be critical for the binding of AMPA receptors to GRIP (Dong et al., Nature 386:279–284 (1997)), ABP (AMPA binding protein, also designated GRIP2) (Srivastava et al., Neuron 21:581–591 (1998); Dong et al., J. Neurosci. 19:6930–6941 (1999)), and PICK1 (Xia et al., Neuron 22:179–187 (1999)). GRIP, ABP and PICK1 are PDZ domain proteins which have been shown to be important for the proper targeting and scaffolding of AMPA receptors to the postsynaptic density (Craven et al., Cell 83:495–498 (1998); O'Brien et al., Curr. Opin. Neurobiol. 8:364–369 (1998)).

To determine whether GPR10 interacts with these proteins, incremental amounts of Flag-tagged GPR10 cDNA, or Flag-tagged GPR10 cDNA with C-terminal mutations, were transiently co-transfected by calcium phosphate transfection with fixed amounts of cDNA encoding GRIP, myc-tagged ABP myc-tagged PSD95, or myc-tagged PICK1 in HEK 293T cells. Flag-tag and C-terminal mutations were introduced by PCR into GPR10 cDNA in pcDNA (Brian O'Dowd, U. Toronto), and sequences were confirmed by dideoxy cycle sequencing containing deaza-dGTP on an ALF-Express automated sequencer (Pharmacia). Myc-PICK1 was generated by PCR using PICK-1 Flag (Jeff Staudinger, GlaxoWellcome) as the template. GRIP cDNA in pRK/CMV was obtained from Richard Huganir (Johns Hopkins), and PSD-95 myc was obtained from Morgan Sheng (Harvard University).

Forty-eight hours after transfection, cells were washed once in PBS and lysed with IP buffer (1% triton X-100, 25 mM Tris, pH 7.4, 50 mM NaCl, 5 mM EDTA, 5 mM EGTA, 0.1 mM phenylmethylsulphonyl fluoride (PMSF), aprotinin, leupeptin, and bacitracin). Immunoprecipitation was performed using 2 μg anti-Flag M2 antibody (Sigma) or 1 μg anti-myc antibody (Roche) followed by 25 μl protein G-agarose (Sigma). Immunoprecipitation was carried out overnight at 4° C. Immunoprecipitated proteins were resolved on SDS-PAGE, transferred to PVDF membrane. Western blotting was performed to detect GRIP using anti-GRIP antibody (1:1000). ABP-myc, PSD-95-myc, and PICK1-myc were detected using the monoclonal anti-myc antibody (1:500, Clontech).

As shown in FIG. 2B, increasing amounts of GRIP were co-immunoprecipitated with GPR10 as the amount of co-transfected GPR10 increased. The specificity of this interaction was demonstrated by introducing mutations at the COOH-terminal tail of Flag-tagged GPR10 (FIG. 2C). Deletion of the last six amino acids, as well as substituting the last 4 amino acids with unrelated sequences completely abolished GRIP co-immunoprecipitation (FIG. 2D). Furthermore, alanine point mutations were introduced in place of each of the last six amino acids and revealed that threonine-365, valine-366, and valine-369 were not important for GRIP interaction, while serine-367, valine-368, and isoleucine-370 were critical (FIG. 2D), consistent with results of similar studies performed with AMPA receptors (Dong et al., Nature 386:279–284 (1997); Srivastava et al., Neuron 21:581–591 (1998)).

These results indicate that the C-terminal tail of GPR10 contains a sequence that can interact with GRIP or GRIP-like proteins.

GRIP is a large cytoplasmic protein containing seven PDZ domains. A previous study has shown that GluR2 and GluR3 interact with the central three PDZ domains of GRIP (domains 4–6) (Dong et al., Nature 386:279–284 (1997)). To determine whether GPR10 interacts with the same domains, 6X-Histidine tagged GRIP PDZ domain segments 1–3, 4–6 or 7, generated by PCR, were co-transfected and immuno-precipitated with Flag-tagged GPR10. As shown in FIG. 2E, GPR10 interacted with PDZ domains 4–6 of GRIP. This interaction is specific, since the C-terminally deleted GPR10 mutant (del6) was unable to interact.

Besides GRIP, other PDZ domain-containing proteins have been demonstrated to interact with the same C-terminal residues of AMPA receptors. To determine whether GPR10 interacts specifically with AMPA receptor interacting proteins, myc-tagged ABP and myc-tagged PSD95 were transfected into cell lines expressing wild type and mutant Flag-tagged GPR10. As shown in FIG. 2F, GPR10 interacted with the AMPA receptor binding protein ABP, but not with PSD95, a PDZ domain protein important for NMDA receptor trafficking to and anchoring at glutaminergic synapses (Gomperts, Cell 84:659–662 (1996)).

Figure 3:
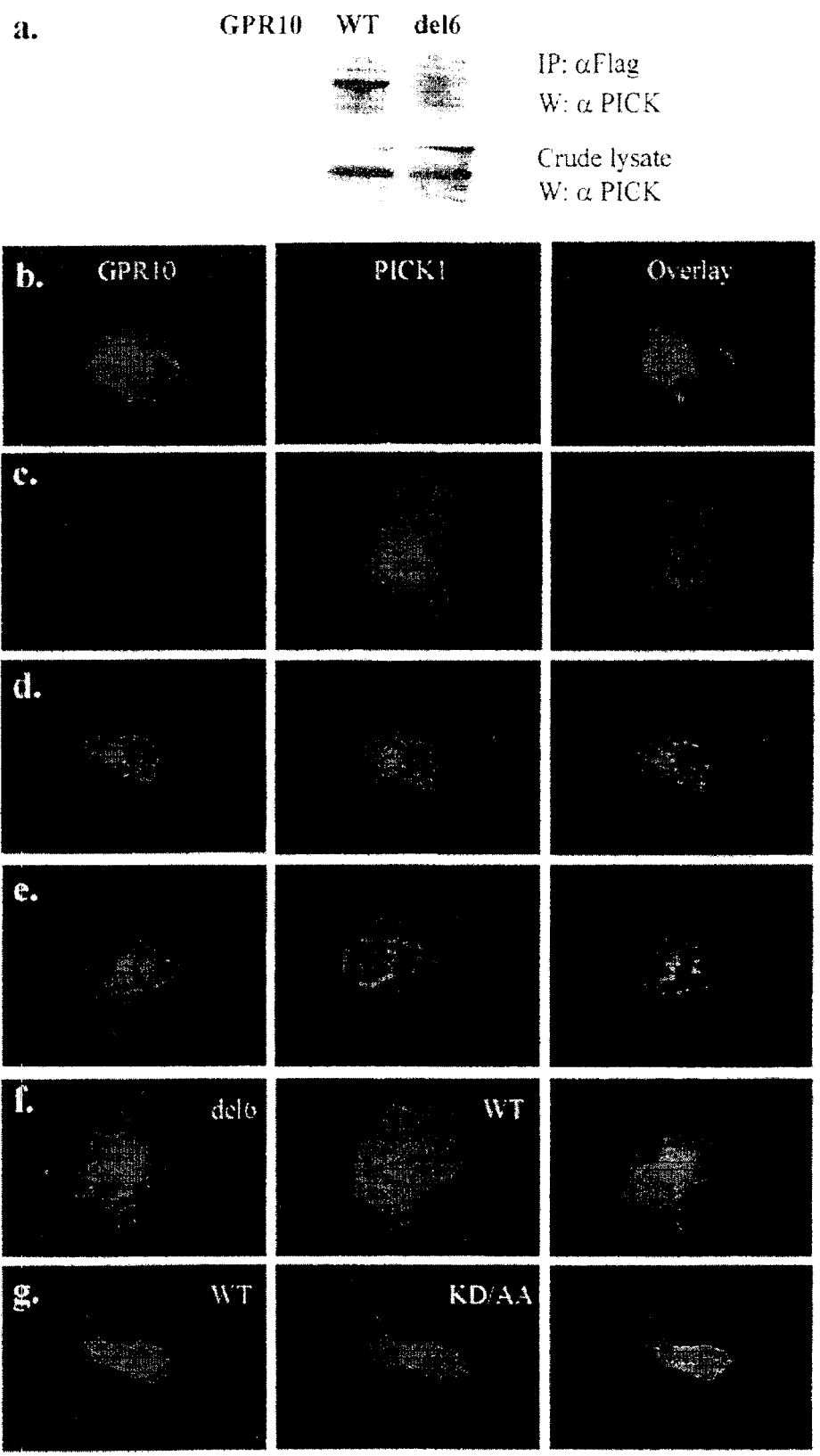
FIG. 3A shows an analysis of co-immunoprecipitation of myc-tagged PICK1 and Flag-tagged GPR10 from cotransfected HEK 293T cells.
FIG. 3B shows the expression pattern of GPR10 in COS7 cells transfected with GPR10 alone.
FIG. 3C shows the expression pattern of PICK1 in COS7 cells transfected with PICK1 alone.
FIG. 3D shows cytoplasmic clusters of GPR10 and PICK1 in COS7 cells co-transfected with GPR10 and PICK1.
FIG. 3E shows cell surface clusters of GPR10 and PICK1 in COS7 cells co-transfected with GPR10 and PICK1.
FIG. 3F shows the expression pattern of a GPR10 mutant (del6) and PICK1 in COS7 cells co-transfected with GPR10 (del6) and PICK1.
FIG. 3G shows the expression pattern of GPR10 and a PICK1 mutant (KD/AA) in COS7 cells co-transfected with GPR10 and PICK1 (KD/AA).

PICK1, originally identified as a PKCα interacting protein (Staudinger et al., J. Biol. Chem. 272:32019–32024 (1997)), is another PDZ domain protein recently shown to interact with the GluR2 subunit of AMPA receptors. Unlike GRIP and ABP, PICK1 is the only AMPA receptor interacting protein that forms intracellular and surface aggregates with GluR2 subunits (but not GluR1) in heterologous cell lines (Xia et al., Neuron 22:179–187 (1999); Dev et al., Neuropharmacology 38:635–644 (1999)). To determine whether GPR10 could mimic these characteristics, co-immunoprecipitation was performed on cells co-transfected with myc-tagged PICK1 and Flag-tagged GPR10. As shown in FIG. 3A, immunoprecipitation of GPR10 caused a concomitant precipitation of PICK1 protein, an effect which was not observed using the mutant (del6) receptor.

Immunocytochemistry was also performed as follows. COS7 cells were transfected with LipofectAMINE (Gibco-BRL) using 6 μg DNA. Twenty-four hours after transfection, cells were trypsinized and seeded onto poly-D-lysine coated glass coverslips. All immunocytochemical analysis was done 48 hours after transfection. Anti-PICK1 antibody (1:500) was incubated overnight at 40° C., whereas anti-myc monoclonal antibody (1:500, Clontech) was incubated for 2 hours at room temperature. All chromophore conjugated secondary antibodies were incubated for 1 hour at room temperature. Coverslips were mounted on Vectashield mounting media (Vector laboratories), and visualized at 60 X on a Nikon fluorescence microscope.

COS7 cells transfected with either GPR10 and PICK1 alone exhibited diffuse cytoplasmic staining, as shown in FIGS. 3B and 3C. However, cells co-expressing both proteins exhibited intracellular (FIG. 3D) as well as surface clustering (FIG. 3E) of GPR10 and PICK1. Such clustering is contingent upon direct protein-protein interaction between the COOH-terminal residues of GPR10 and the PDZ domain of PICK1, since deleting the last six residues of GPR10 as well as mutating critical residues within the PDZ domain of PICK1 (K27D28AA) (Staudinger et al., *J. Biol. Chem.* 272:32019–32024 (1997)) obliterates clustering (FIGS. 3F and 3G).

These results strongly support the possibility that GRIP-like molecules, besides interacting with AMPA receptors at the postsynaptic density, could help,recruit molecules such as GPR10 and PKC to form a signal transduction complex with AMPA receptors. The assembly of such proteins in microdomains forms an efficient network by which activation of one protein could modulate other proteins in the complex.

Examples of G-protein coupled receptors (GPCRs) affecting channel function through direct or indirect interactions with PDZ domain proteins have been reported. For instance, the β2 adrenergic receptor (β2AR) indirectly activates the $Na^+/H^+$ exchanger (NHE3) by binding to the PDZ domain protein NHERF, which normally inhibits NHE3 activity (Hall et al., *Nature* 392:626–630 (1998)). This interaction is mediated through the COOH-terminal sequence of β2AR in an agonist dependent manner. Drosophila rhodopsin indirectly affects $Ca^{++}$ influx through a TRP calcium channel via a Gq/PLC/eye PKC phototransduction cascade organized by the PDZ domain protein inaD (Tsunoda et al., *Nature* 388:243–249 (1997)). Finally, the CRF-Rl receptor has also been shown to interact with PSD95 through an analogous COOH terminal motif found also in NR2 subunits of NMDA receptors (Gaudriault et al., *Society for Neuroscience Abstract* 24:570 (1998)).

EXAMPLE III

Effect of PrRP on Thalamic Oscillatory Activity

This example shows that PrRP reduces AMPA receptor-mediated, but not NMDA receptor-mediated, thalamic oscillatory activity.

Given that GPR10 interacts with AMPA receptor associated molecules it was postulated that GPR10 receptor activation may affect AMPA receptor signaling. Such an effect would most likely influence oscillatory activity produced in the RTN since glutamatergic inputs are critical for maintaining this network function (Salt et al., *Prog. Neurobiol.* 48:55–72 (1996)). To test this hypothesis, extracellular recordings were made from the RTN in thalamic slices.

Horizontal thalamic slices (400 μm) were prepared from Sprague-Dawley rats (postnatal rats 13–15) using a vibratome (Leica, VT1OOOS). The slices were transferred to a recording chamber after at least 1 hr recovery, and were superfused with artificial cerebrospinal fluid (aCSF) equilibrated with 95% $O_2$/5% $CO_2$ at 0.5 ml/mm. The aCSF contained (in mM): NaCl 126, KCl 2.5, $NaH_2PO_4$ 1.25, $CaCl_2$ 2, $MgSO_4$ 0.63, $NaHCO_3$ 26, and glucose 10. All experiments were carried out in the presence of 10 μM bicuculline maleate and cytochrome c (100 μg/ml) at 34° C. A glass electrode filled with 2 M NaCl was positioned in the nucleus of reticular thalamus (RTN), and extracellular recording was made in response to stimulation of the internal capsule (1–50 μA) every 20–30 sec. After establishing stable oscillatory activity, PrRP was applied for 15–20 min. Paired Student's t-Test was used for statistical analysis. The data were digitized at 1–5 kHz with the Neuronal Activity Acquisition Program (Eclectek Enterprise).

Figure 4:
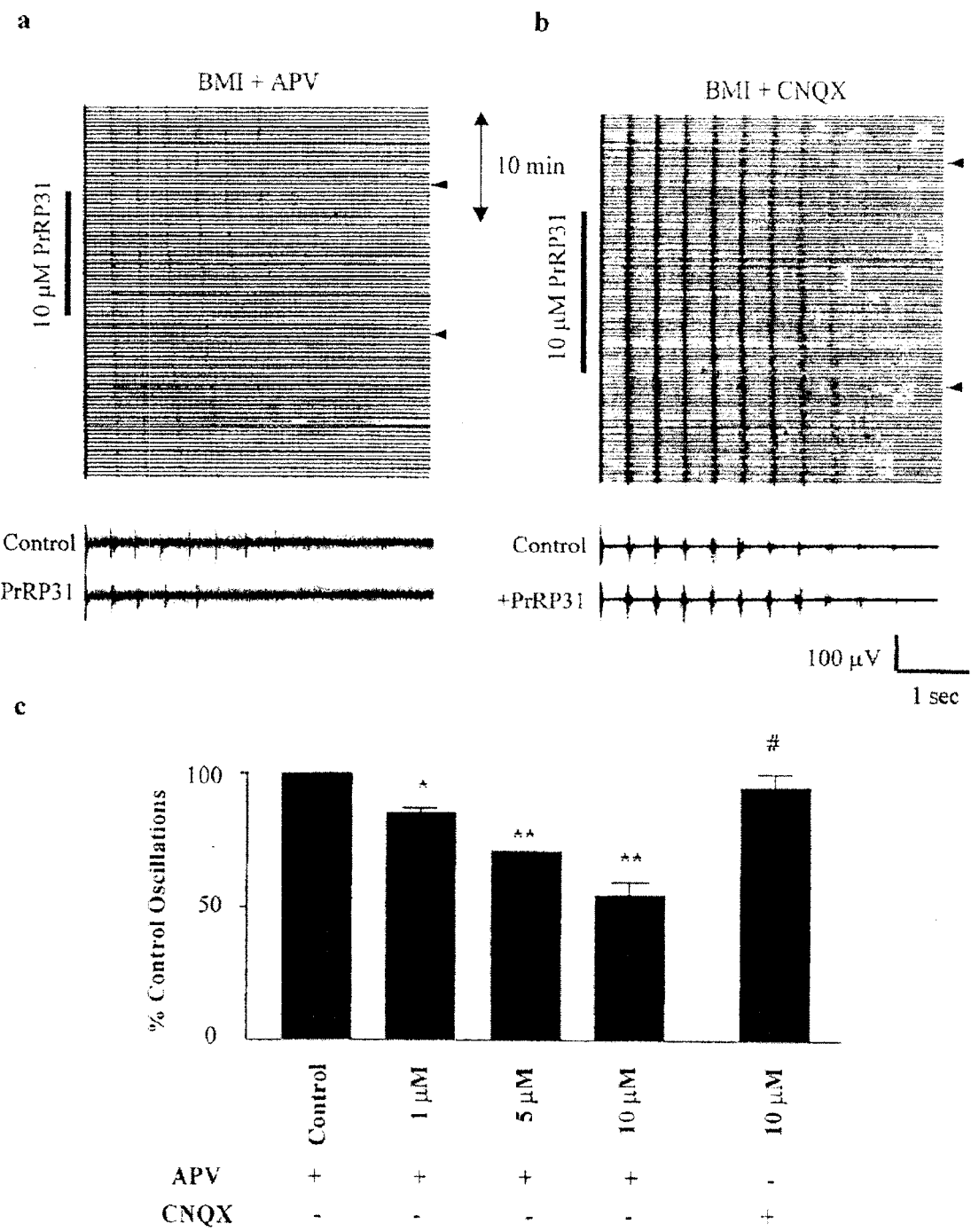
FIG. 4A shows the effect of PrRP on AMPA receptor-mediated thalamic oscillatory activity.
FIG. 4B shows the effect of PrRP on NMDA receptor-mediated thalamic oscillatory activity.
FIG. 4C shows the concentration dependent effect of PrRP on thalamic oscillatory activity. *, $p<0.01$; **, $p<0.001$, paired Student's t-Test.

In the representative experiments shown in FIG. 4, each block shows 90–100 sweeps of 5 set duration, separated by 20–30 set, and each sweep represents the oscillatory activity in response to a single stimulation pulse delivered to the internal capsule. The bar on the left indicates the duration of peptide application. The traces at the bottom show representative responses before and in the presence of PrRP, taken at the time points indicated with arrow heads.

Under $GABA_A$ receptor blockade and reduced $Mg^{2+}$, stimulation of the internal capsule induced 4–12 spindle-like discharges oscillating at 3–4 Hz (FIG. 4), as previously reported (Ulrich et al., *Neuron* 15,909–918 (1995)). In order to isolate the AMPA receptor driven-oscillation, slices were equilibrated with the NMDA receptor antagonist D,L-aminophosphonovaleric acid (DL-APV).

Application of PrRP significantly reduced the number of oscillations (FIG. 4A) and the effect was concentration dependent (FIG. 4C). Maximum suppression, approximately 40%, was obtained at 10 μM since higher concentrations (20 μM) produced a comparable degree of inhibition. In the experiments depicted in FIG. 4C, the number of oscillations in the presence of PrRP was normalized to that of the pre-peptide response. Columns represent the mean+/–S.E. of 12 (pre-peptide), 6 (10 μM), 2 (5 μM), and 4 (1 μM) experiments, respectively.

It was next investigated whether the suppression of RTN oscillatory activity by PrRP is the consequence of AMPA receptor modulation or some general cellular effect. If the latter, thalamic oscillations driven by NMDA receptors should be similarly reduced by PrRP. The above experiment was thus repeated in a low $Mg^{2+}$ (0.1 mM)-aCSF containing 10 μM of the AMPA receptor antagonist CNQX. As shown in FIGS. 4B and 4C (right column, n=4), 10 μM PrRP had no discernible effect on oscillation under these circumstances.

In summary, the results described in this example indicate that PrRP reduces thalamic oscillatory activity by selectively modulating AMPA receptors.

EXAMPLE IV

Effect of PrRP on Absence Seizures

This example shows that PrRP suppresses seizure activity in GAERS.

Spindle wave oscillations generated in the brain slice correlate well with the activity seen during slow wave sleep as well as during an episode of absence seizure attack (Danober et al., *Prog. Neurobiol.* 55:27–57 (1998); McCormick et al., *Annu. Rev. Neurosci.* 20:185–215 (1997)). To assay whether the in vitro effects of PrRP on thalamic oscillations reflect in vivo efficacy, an animal model of absence seizure that present with spontaneous spike-and-wave discharges (SWD) was used.

The GAERS (Genetic Absence Epilepsy Rats from Strasbourg) is a rat strain that exhibits recurrent seizure activity characterized by bilateral and synchronous SWD and behavioral arrest (Danober et al., *Prog. Neurobiol.* 55:27–57 (1998)). Drugs used to treat absence seizure in humans have been shown to be effective in suppressing seizure activity in this model (Danober et al., *Prog. Neurobiol.* 55:27–57 (1998); Gower et al., *Epilepsy Res.* 22:207–213 (1995)).

Electroencephalogram (EEG) recordings and intracerebroventricular (ICV) injection into GAERS were performed essentially as described in Liu et al., Brain Res. 545:1–7 (1991). Briefly, six male GAERS (300–400 g) were implanted stereotaxically (AP=–0.8, ML=1.2, CV=3 mm, with bregma as reference) with a permanent stainless steel cannula under pentobarbital anesthesia (40 mg/kg i.p.). All rats were also implanted bilaterally with 4 stainless-steel electrodes at the frontal and parietal cortex and connected to a microconnector. Both the guide cannulae and EEG electrodes were anchored to the skull using retaining screws and dental acrylic cement.

After one week of recovery, stainless steel injection cannulae were introduced into the guide cannulae so as to extend 2–4 mm beyond their tips. Injection cannulae were connected to a 10 µl microsyringe driven by a pump. Five microliters saline or peptides at various concentrations were microinjected over 1 min through the cannulae while taking EEG recordings continuously throughout the duration of the experiment, in freely moving animals. During EEG recordings the rats were carefully watched and were prevented from falling asleep by gentle sensory stimulation. Seizure frequency was determined as a cumulative duration of spike and wave discharges per consecutive 20 minute periods (seconds of seizure activity per 20 minute recording) after the initial injection. Statistical analysis was performed using the Wilcoxon test.

Figure 5:
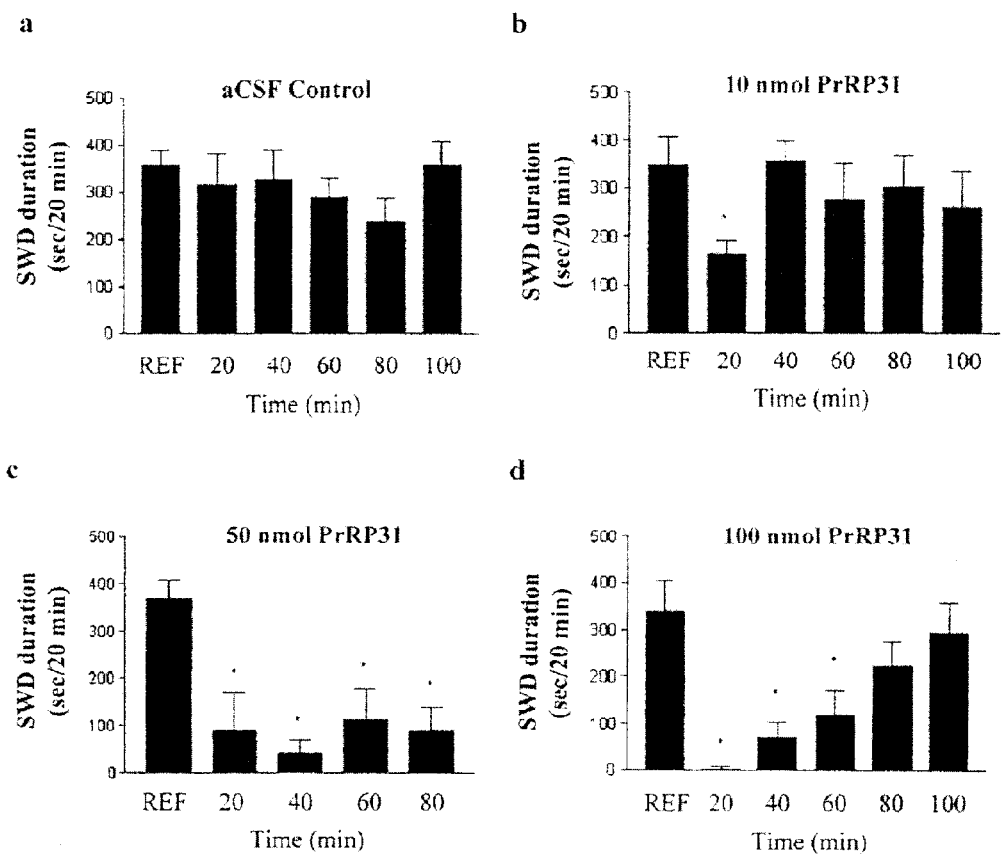
FIG. 5 shows seizure frequency in GAERS rats (n=6), expressed as cumulative duration of spike and wave discharges (SWD) at 20 min intervals after injection of aCSF control (FIG. 5A) or injection of various PrRP concentrations (FIGS. 5B–D). "REF"=reference duration of spontaneous seizure activity before injection.

PrRP was administered intracerebroventricularly into GAERS rats. EEG was taken throughout the course of the experiment and time spent in seizures (spike and wave discharges (SWD) duration) was tabulated for 20 minute intervals from the initial infusion of either aCSF control or various peptide concentrations. Data from six animals receiving the same treatment were pooled. In comparison to aCSF control, PrRP was able to dose-dependently suppress seizure activity in this animal model (FIGS. 5A–5D). At 10 nmol PrRP, the SWD duration was reduced by half for the first 20 minutes, and returned to baseline after 40 minutes (FIG. 5B). At higher peptide concentrations, seizure activity was reduced more significantly (i.e. by 75% at 50 nmol (FIG. 5C), and by almost 100% at 100 nmol at 20 minutes (FIG. 5D)). This seizure suppressing activity remained significant 60 to 80 minutes after peptide injection. No other mobility or behavioral changes were observed at all peptide concentrations.

FIG. 6 also shows that PrRP suppresses absence seizure activity in GAERS. FIG. 6A shows a bilateral frontoparietal EEG recording, which shows spike and wave discharges in a GAERS prior to treatment with PrRP. FIG. 6B shows changes in EEG pattern after i.c.v. injection of PrRP (100 nmol). The chart calibration was 200 microV/1 sec. FIG. 6C shows cumulative duration of spike and wave discharges per 20 min epoch in GAERS (mean±S.E.M.) before injection (Ref) and 20, 40, and 60 min after injection of vehicle or 10, 50, or 100 nmol PrRP. *P<0.001.

The results described above demonstrate that PrRP is effective in suppressing absence seizures.

In summary, the results described in Examples I–IV demonstrate that GPR10, the PrRP receptor, is highly expressed in the GABAergic neurons of the RTN; that GPR10 contains structural motifs that allow it to interact with PDZ domain-containing proteins; that application of PrRP specifically reduces AMPA receptor mediated oscillatory activity; and that PrRP suppresses absence seizures. These results show a novel role of GPR10 and PrRP in regulating thalamic networks and implicate GPR10 as a potential therapeutic target in the treatment of disorders associated with the RTN, including absence seizures and sleep disorders.

EXAMPLE V

Whole Cell Electrophysiological Recordings from RTN Neurons

This example shows an exemplary method of determining the ability of a compound to modulate AMPA receptor signaling.

Horizontal slices (200 µm) are prepared from postnatal Sprague Dawley rats (P13–P15). After at least one hour of incubation at room temperature in artificial cerebrospinal fluid (aCSF) containing (in mM): NaCl 126, KCl 2.5, $NaH_2PO_4$ 1.25, $CaCl_2$ 2, $MgSO_4$ 2, $NaHCO_3$ 26, and glucose 10), slices are transferred to a recording chamber and submerged in low $Mg^{2+}$-aCSF (0.63 mM) equilibrated with 95% $O_2$/5% $CO_2$. Whole cell recording are made from neurons in the nucleus of reticular thalamus at room temperature in low $Mg^{2+}$-aCSF containing 100 mM DL 2-aminophosphonovaleric acid (APV), 10 mM bicuculline maleate (BMI), and 100 mg/ml cytochrome c. The flow rate is 2 ml/min. Patch electrodes are pulled from borosilicate glass (2–3 MOhm) and filled with a pipette solution containing (in mM): CsCl 135, MgCl 2, EGTA 10, HEPES 10, ATP 10, and QX314 5 (pH 7.3). Excitatory postsynaptic currents (EPSCs) are recorded in response to activation of the internal capsule. The holding current and access resistance are constantly monitored and the holding potential is maintained at –70 mV throughout the experiment. After establishing a stable baseline, a compound is applied to the perfusion line for 15 minutes. The data is digitized and analyzed offline. Aspects of the method are described in further detail in Cox et al., J. Neurophysiol. 74:990–1000 (1995).

EXAMPLE VI

Whole Cell Ion Influx Assays

This example shows a further exemplary method of determining the ability of a compound to modulate AMPA receptor signaling.

The method uses cells that express both AMPA receptors and PrRP receptors, such as cell lines (e.g. HEK 293 cells) transiently or stably transfected with AMPA receptors and GPR10, or RTN neurons. A determination is made as to effect of the test compound on calcium ion or sodium ion influx in response to AMPA receptor agonists. The method is amenable to either low-throughput (e.g. light microscopy) or high-throughput (e.g. FLIPR) assays.

AMPA receptor agonists include, for example, AMPA (e.g. s-AMPA zwitterion, at a concentration of about 10 µM) or glutamate (at a concentration of about 10 mM). Optionally, an assay can be performed in the presence of an AMPA receptor antagonist (e.g. CNQX at a concentration of about 20 µM), for example to ensure that any response is dependent on AMPA receptors. Since AMPA receptors desensitize rapidly upon activation, a drug such as cyclothiazide can be added, at a concentration of about 100 µM. The addition of cyclothiazide is expected to reduce the desensitization rate and potentiate AMPA signals by a factor of about 200 fold. The use of such antagonists and modulators to isolate or stabilize AMPA signals are well known in the art.

To determine whether PrRP receptor agonist or antagonist modulates AMPA receptor signaling, the test compound is added to the cells, followed by an AMPA receptor agonist. The relative amplitude change of calcium or sodium influx through the AMPA receptors is a measure of the ability of the compound to modulate AMPA receptor signaling.

In calcium ion influx assays, PrRP can be added to the cells for a sufficient period (e.g. about 3 to 5 minutes) to desensitize GPR10-mediated calcium signals and more clearly determine specific AMPA receptor mediated signals. Calcium channels can be blocked, if desirable, with calcium channel blockers known in the art. Calcium ion influx in response to AMPA receptor activation can be determined using fluorescent sensitive calcium indicators (e.g. Fluo-3 and the like), by visualizing single cells under light microscopy. Alternatively, particularly where high-throughput screening is desired, calcium influx in response to AMPA receptor activation can be determined using a fluorometric imaging plate reader (FLIPR), which allows rapid detection of changes in intracellular calcium levels.

Likewise, sodium ion influx in response to AMPA receptor activation can be determined using fluorescent sensitive sodium indicators (e.g. SBFI and the like, available from Molecular Probes), either by visualizing single cells under light microscopy or by adapting FLIPR technology.

EXAMPLE VII

PrRP Induces Waking and Suppresses Slow Wave Sleep in Rats

This example shows the PrRP induces waking and suppresses slow wave activity in sleeping animals.

To determine if PrRP modulates sleep/wake or arousal states, varying doses of PrRP were injected i.c.v. into sleeping rats. EEG and EMG were recorded for 150 min in three groups, each consisting of 6 rats, that received either vehicle, 1 nmol PrRP, or 10 nmol PrRP. Analyses were conducted across five consecutive 30-min epochs; vehicle or PrRP were injected at the end of the second epoch. Vehicle-treated rats spent a substantial portion of the entire testing period asleep with characteristic EEG/EMG recordings. EEG and EMG recordings were made from Male Sprague-Dawley rats (300–400 g, Sasco, Oregon, Wis.) according to the method described previously (Berridge et al., *J. Neurosci.*, 16:6999–7009 (1996)).

Rats were housed in pairs for at least 7-days prior to surgery with ad lib access to food and water on an 11:13 hour light:dark cycle (lights on 7:00 a.m.). Approximately 5 μl of vehicle or PrRP31 dissolved in vehicle (1 nmol/2 ml; 10 nmol/2 ml) was infused intracerebroventricularly through a pre-implanted cannula (Berridge et al., supra (1996)). Artificial extracellular fluid (147 mM NaCl, 1.3 mM $CaCl_2$, 0.9 mM $MgCl_2$, 2.5 mM KCl, 5.0 mM $NaH_2PO_4$; pH 7.4) plus 200 μg/ml cytochrome c served as vehicle. Infusions were made over a 2-min period using a microprocessor-controlled infusion pump (Harvard Apparatus, South Natick, Mass.). Cortical EEG (ECoG) from the frontal cortex and EMG from the dorsal neck muscles were recorded for 60 min prior to infusion and 90 min following infusion. To be scored as a distinct epoch, the appropriate ECoG and EMG activity patterns needed to persist for a minimum of 15 sec. Time spent in each state was scored and totaled for the five 30 min epochs of the observation period, two during the preinfusion period and three during the post-infusion period. The location of the infusion needle was verified morphologically after each experiment. Data were only used for analysis when EEG recordings were electrically adequate and infusion needle placement was accurate. Statistical analysis was performed using a two-way mixed-design ANOVA with drug treatment as the between-subjects variable and time as the within-subjects variable. Post-hoc analyses were conducted using Tukey's HSD test.

FIG. 7A shows representative EEG/EMG traces of pre- and post-injection effects of PrRP (10 nmol) on sleeping animals. FIG. 7A indicates that infusion of PrRP elicited dose-dependent increases in the EEG/EMG indices of waking. FIGS. 7B and 7C show the effects of varying concentrations of PrRP infused into the lateral ventricle on total time spent awake (FIG. 7B) and slow-wave slept (FIG. 7C). Symbols represent mean±SEM of the time (sec) spent in the two different behavioral state categories of six animals per 30-min epoch. PRE1 and PRE2 represent pre-infusion epochs. POST1–POST3 represent post-infusion epochs. Vehicle-treated rats spent a substantial proportion of the testing period asleep. Total time spent awake was significantly increased during the POST1 and POST2 epochs in the 10 nmol group.

FIG. 7B shows that PrRP significantly increased total time spent awake (treatment, $F_{(2,15)}=24.4$, $p<0.001$; time, $F_{(4,60)}=19.5$, $p<0.001$; treatment×time, $F_{(8,60)}=8.4$, $p<0.001$) and accordingly, decreased total time spent asleep (slow-wave sleep+REM sleep), as shown in FIG. 7C. Post hoc analyses indicate that total time spent awake was significantly increased during post-infusion epochs in rats treated with 10 nmol PrRP with only a trend at the 1 nmol dose. FIG. 7C shows that the increase in awake time at the higher dose was mirrored in the near-complete suppression of slow-wave sleep (treatment, $F_{(2,15)}=20.7$, $p<0.001$).

In summary, PrRP, when injected into animals during their sleep phase, induced a robust change in the EEG/EMG patterns. Slow wave sleep characterized by high amplitude, low frequency waves and a silent EMG was replaced within minutes by normal waking patterns, and the animals exhibited visible behavioral indices of waking. Conversion to the awake state was nearly complete at a dose of 10 nmol and lasted for well over an hour.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. A method of screening for a compound for promoting wakefulness in a mammal, comprising:
   (a) contacting a PrRP receptor with one or more candidate compounds under conditions wherein PrRP promotes interaction of PrRP receptor with an AMPA receptor associated protein;
   (b) identifying a compound that promotes said interaction;
   (c) providing said compound, and
   (d) determining the ability of said compound to promote wakefulness.

2. The method of claim 1, wherein said AMPA receptor associated protein is selected from the group consisting of GRIP, GRIP2 and PICK1.

3. The method of claim 1, wherein the ability of said compound to promote wakefulness is determined by a method selected from the group consisting of EEG measurement, EMG measurement and wake time measurement.

4. The method of claim 1, wherein the ability of said compound to promote wakefulness is determined by administering said compound to a mammal selected from the group consisting of a human, a non-human primate, rat and a mouse.

* * * * *

SEQUENCE LISTING

<160> NUMBER OF SEQ ID NOS: 24

<210> SEQ ID NO 1
<211> LENGTH: 29
<212> TYPE: PRT
<213> ORGANISM: Homo Sapien

```
<400> SEQUENCE: 1

Phe Arg Glu Glu Leu Arg Lys Leu Leu Val Ala Trp Pro Arg Lys Ile
 1               5                  10                  15

Ala Pro His Gly Gln Asn Met Thr Val Ser Val Val Ile
            20                  25

<210> SEQ ID NO 2
<211> LENGTH: 29
<212> TYPE: PRT
<213> ORGANISM: Homo Sapien

<400> SEQUENCE: 2

Asn Pro Ser Ser Ser Gln Asn Ser Gln Asn Phe Ala Ala Thr Tyr Lys
 1               5                  10                  15

Glu Gly Tyr Asn Tyr Tyr Gly Ile Glu Ser Val Lys Ile
            20                  25

<210> SEQ ID NO 3
<211> LENGTH: 29
<212> TYPE: PRT
<213> ORGANISM: Homo Sapien

<400> SEQUENCE: 3

Phe Lys Pro Ala Pro Ala Thr Asn Thr Gln Asn Tyr Ala Thr Tyr Arg
 1               5                  10                  15

Glu Gly Tyr Asn Val Tyr Gly Thr Glu Ser Val Lys Ile
            20                  25

<210> SEQ ID NO 4
<211> LENGTH: 12
<212> TYPE: PRT
<213> ORGANISM: Homo Sapien

<400> SEQUENCE: 4

Pro His Gly Gln Asn Met Thr Val Ser Val Val Ile
 1               5                  10

<210> SEQ ID NO 5
<211> LENGTH: 6
<212> TYPE: PRT
<213> ORGANISM: Artificial Sequence
<220> FEATURE:
<223> OTHER INFORMATION: human GPR10  variant

<400> SEQUENCE: 5

Pro His Gly Gln Asn Met
 1               5

<210> SEQ ID NO 6
<211> LENGTH: 12
<212> TYPE: PRT
<213> ORGANISM: Artificial Sequence
<220> FEATURE:
<223> OTHER INFORMATION: human GPR10 variant

<400> SEQUENCE: 6

Pro His Gly Gln Asn Met Thr Val Pro Arg Pro Ala
 1               5                  10

<210> SEQ ID NO 7
<211> LENGTH: 12
<212> TYPE: PRT
<213> ORGANISM: Artificial Sequence
```

-continued

```
<220> FEATURE:
<223> OTHER INFORMATION: human GPR10  variant

<400> SEQUENCE: 7

Pro His Gly Gln Asn Met Ala Val Ser Val Val Ile
 1               5                   10

<210> SEQ ID NO 8
<211> LENGTH: 12
<212> TYPE: PRT
<213> ORGANISM: Artificial Sequence
<220> FEATURE:
<223> OTHER INFORMATION: human GPR10 variant

<400> SEQUENCE: 8

Pro His Gly Gln Asn Met Thr Ala Ser Val Val Ile
 1               5                   10

<210> SEQ ID NO 9
<211> LENGTH: 12
<212> TYPE: PRT
<213> ORGANISM: Artificial Sequence
<220> FEATURE:
<223> OTHER INFORMATION: human GPR10  variant

<400> SEQUENCE: 9

Pro His Gly Gln Asn Met Thr Val Ala Val Val Ile
 1               5                   10

<210> SEQ ID NO 10
<211> LENGTH: 12
<212> TYPE: PRT
<213> ORGANISM: Artificial Sequence
<220> FEATURE:
<223> OTHER INFORMATION: human GPR10  variant

<400> SEQUENCE: 10

Pro His Gly Gln Asn Met Thr Val Ser Ala Val Ile
 1               5                   10

<210> SEQ ID NO 11
<211> LENGTH: 12
<212> TYPE: PRT
<213> ORGANISM: Artificial Sequence
<220> FEATURE:
<223> OTHER INFORMATION: human GPR10 variant

<400> SEQUENCE: 11

Pro His Gly Gln Asn Met Thr Val Ser Val Ala Ile
 1               5                   10

<210> SEQ ID NO 12
<211> LENGTH: 12
<212> TYPE: PRT
<213> ORGANISM: Artificial Sequence
<220> FEATURE:
<223> OTHER INFORMATION: human GPR10 variant

<400> SEQUENCE: 12

Pro His Gly Gln Asn Met Thr Val Ser Val Val Ala
 1               5                   10

<210> SEQ ID NO 13
<211> LENGTH: 31
<212> TYPE: PRT
<213> ORGANISM: Bos taurus
```

-continued

```
<400> SEQUENCE: 13

Ser Arg Ala His Gln His Ser Met Glu Ile Arg Thr Pro Asp Ile Asn
 1               5                  10                  15

Pro Ala Trp Tyr Ala Gly Arg Gly Ile Arg Pro Val Gly Arg Phe
            20                  25                  30

<210> SEQ ID NO 14
<211> LENGTH: 31
<212> TYPE: PRT
<213> ORGANISM: Rattus

<400> SEQUENCE: 14

Ser Arg Ala His Gln His Ser Met Glu Thr Arg Thr Pro Asp Ile Asn
 1               5                  10                  15

Pro Ala Trp Tyr Thr Gly Arg Gly Ile Arg Pro Val Gly Arg Phe
            20                  25                  30

<210> SEQ ID NO 15
<211> LENGTH: 31
<212> TYPE: PRT
<213> ORGANISM: Homo Sapien

<400> SEQUENCE: 15

Ser Arg Thr His Arg His Ser Met Glu Ile Arg Thr Pro Asp Ile Asn
 1               5                  10                  15

Pro Ala Trp Tyr Ala Ser Arg Gly Ile Arg Pro Val Gly Arg Phe
            20                  25                  30

<210> SEQ ID NO 16
<211> LENGTH: 20
<212> TYPE: PRT
<213> ORGANISM: Bos taurus

<400> SEQUENCE: 16

Thr Pro Asp Ile Asn Pro Ala Trp Tyr Ala Gly Arg Gly Ile Arg Pro
 1               5                  10                  15

Val Gly Arg Phe
            20

<210> SEQ ID NO 17
<211> LENGTH: 20
<212> TYPE: PRT
<213> ORGANISM: Rattus

<400> SEQUENCE: 17

Thr Pro Asp Ile Asn Pro Ala Trp Tyr Thr Gly Arg Gly Ile Arg Pro
 1               5                  10                  15

Val Gly Arg Phe
            20

<210> SEQ ID NO 18
<211> LENGTH: 20
<212> TYPE: PRT
<213> ORGANISM: Homo Sapien

<400> SEQUENCE: 18

Thr Pro Asp Ile Asn Pro Ala Trp Tyr Ala Ser Arg Gly Ile Arg Pro
 1               5                  10                  15

Val Gly Arg Phe
            20
```

```
<210> SEQ ID NO 19
<211> LENGTH: 7
<212> TYPE: PRT
<213> ORGANISM: Artificial Sequence
<220> FEATURE:
<223> OTHER INFORMATION: human  PrRP variant
<221> NAME/KEY: VARIANT
<222> LOCATION: (1)...(7)
<223> OTHER INFORMATION: Xaa = Any Amino Acid

<400> SEQUENCE: 19

Xaa Arg Pro Val Gly Arg Phe
 1               5

<210> SEQ ID NO 20
<211> LENGTH: 7
<212> TYPE: PRT
<213> ORGANISM: Artificial Sequence
<220> FEATURE:
<223> OTHER INFORMATION: human  PrRP variant
<221> NAME/KEY: VARIANT
<222> LOCATION: (1)...(7)
<223> OTHER INFORMATION: Xaa = Any Amino Acid

<400> SEQUENCE: 20

Ile Arg Xaa Val Gly Arg Phe
 1               5

<210> SEQ ID NO 21
<211> LENGTH: 7
<212> TYPE: PRT
<213> ORGANISM: Artificial Sequence
<220> FEATURE:
<223> OTHER INFORMATION: human PrRP variant
<221> NAME/KEY: VARIANT
<222> LOCATION: (1)...(7)
<223> OTHER INFORMATION: Xaa = Any Amino Acid

<400> SEQUENCE: 21

Ile Arg Pro Xaa Gly Arg Phe
 1               5

<210> SEQ ID NO 22
<211> LENGTH: 7
<212> TYPE: PRT
<213> ORGANISM: Artificial Sequence
<220> FEATURE:
<223> OTHER INFORMATION: human PrRP variant
<221> NAME/KEY: VARIANT
<222> LOCATION: (1)...(7)
<223> OTHER INFORMATION: Xaa = Any Amino Acid

<400> SEQUENCE: 22

Ile Arg Pro Val Gly Arg Xaa
 1               5

<210> SEQ ID NO 23
<211> LENGTH: 7
<212> TYPE: PRT
<213> ORGANISM: Homo Sapien

<400> SEQUENCE: 23

Ile Arg Pro Val Gly Arg Phe
 1               5

<210> SEQ ID NO 24
<211> LENGTH: 4
<212> TYPE: PRT
<213> ORGANISM: Homo Sapien
```

-continued

```
<400> SEQUENCE: 24

Ser Val Val Ile
  1
```